US011759165B2

United States Patent
Takada et al.

(10) Patent No.: US 11,759,165 B2
(45) Date of Patent: Sep. 19, 2023

(54) ULTRASOUND DIAGNOSIS APPARATUS AND ANALYZING APPARATUS

(71) Applicant: CANON MEDICAL SYSTEMS CORPORATION, Otawara (JP)

(72) Inventors: Yuko Takada, Utsunomiya (JP); Masaki Watanabe, Utsunomiya (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 0 days.

(21) Appl. No.: 16/857,415

(22) Filed: Apr. 24, 2020

(65) Prior Publication Data

US 2020/0337671 A1  Oct. 29, 2020

(30) Foreign Application Priority Data

Apr. 26, 2019  (JP) ................................. 2019-085456

(51) Int. Cl.
| A61B 8/00 | (2006.01) |
| A61B 8/06 | (2006.01) |
| A61B 8/08 | (2006.01) |

(52) U.S. Cl.
CPC .................. *A61B 8/06* (2013.01); *A61B 8/42* (2013.01); *A61B 8/4461* (2013.01); *A61B 8/463* (2013.01); *A61B 8/5207* (2013.01)

(58) Field of Classification Search
CPC .. A61B 8/06; A61B 8/085; A61B 8/42; A61B 8/4245; A61B 8/4461; A61B 8/463; A61B 8/465; A61B 8/469; A61B 8/5207; A61B 8/5223; A61B 8/44; A61B 8/4444; A61B 8/467; A61B 8/488
See application file for complete search history.

(56) References Cited

U.S. PATENT DOCUMENTS

| 2004/0193053 A1* | 9/2004 | Kato ...................... A61B 8/463 600/440 |
| 2009/0036775 A1 | 2/2009 | Ikuma et al. |
| 2014/0155749 A1 | 6/2014 | Ogasawara |

(Continued)

FOREIGN PATENT DOCUMENTS

| JP | 7-248558 A | 9/1995 |
| JP | 2009-34225 A | 2/2009 |

(Continued)

OTHER PUBLICATIONS

Japanese Office Action dated Sep. 20, 2022 in Japanese Patent Application No. 2019-085456, 7 pages.

(Continued)

*Primary Examiner* — Christopher Koharski
*Assistant Examiner* — Taylor Deutsch
(74) *Attorney, Agent, or Firm* — Oblon, McClelland, Maier & Neustadt, L.L.P.

(57) ABSTRACT

An ultrasound diagnosis apparatus according to an embodiment includes processing circuitry. The processing circuitry is configured to generate moving speed information indicating a moving speed of an ultrasound probe, on the basis of a predetermined number of pieces of medical image data among a plurality of pieces of medical image data in a time series obtained from an ultrasound scan performed by the ultrasound probe. The processing circuitry is configured to cause a display to display the moving speed information.

13 Claims, 16 Drawing Sheets

(56) References Cited

U.S. PATENT DOCUMENTS

| | | | | |
|---|---|---|---|---|
| 2015/0342568 A1* | 12/2015 | Kato | ............... | A61B 8/461 600/443 |
| 2016/0019432 A1 | 1/2016 | Fredenberg et al. | | |
| 2016/0019441 A1* | 1/2016 | Ryu | ............... | A61B 8/085 382/131 |
| 2016/0048737 A1* | 2/2016 | Kam | ............... | A61B 8/4245 382/131 |
| 2016/0171708 A1* | 6/2016 | Kim | ............... | G06T 7/0012 382/128 |
| 2017/0112471 A1* | 4/2017 | Toji | ............... | A61B 8/54 |
| 2018/0028156 A1* | 2/2018 | Matsunaga | ............... | A61B 8/4254 |
| 2019/0388063 A1* | 12/2019 | Oka | ............... | A61B 8/461 |

FOREIGN PATENT DOCUMENTS

| | | | |
|---|---|---|---|
| JP | 5843748 B2 | 1/2016 | |
| JP | 2016-22279 A | 2/2016 | |
| JP | 2016-508409 A | 3/2016 | |
| JP | 2016-51 2776 A | 5/2016 | |
| JP | 2017-60587 A | 3/2017 | |
| JP | 2018-20109 A | 2/2018 | |
| JP | 2019-63483 A | 4/2019 | |
| WO | WO 2014/133605 A1 | 9/2014 | |
| WO | WO-2016013454 A1 * | 1/2016 | ............... A61B 8/14 |

OTHER PUBLICATIONS

Japanese Office Action dated Dec. 13, 2022, in Japanese Patent Application No. 2019-085456, 7 pages.

Decision of Refusal dated Apr. 4, 2023, issued in corresponding Japanese patent application No. 2019-085456.

Decision of Dismissal of Amendment dated Apr. 4, 2023, issued in corresponding Japanese patent application No. 2019-085456.

* cited by examiner

|      | 51_1 | 51_2 | 51_3 | 51_4 | 51_5 |
|------|------|------|------|------|------|
| 52_1 | r11  | r12  | r13  | r14  | r15  |
| 52_2 | r21  | r22  | r23  | r24  | r25  |
| 52_3 | r31  | r32  | r33  | r34  | r35  |
| 52_4 | r41  | r42  | r43  | r44  | r45  |
| 52_5 | r51  | r52  | r53  | r54  | r55  |

|      | 51_1 | 51_2 | 51_3 | 51_4 | 51_5 |
|------|------|------|------|------|------|
| 52_1 | r11  | r12  | r13  | r14  | r15  |
| 52_2 | r21  | r22  | r23  | r24  | r25  |
| 52_3 | r31  | r32  | r33  | r34  | r35  |
| 52_4 | r41  | r42  | r43  | r44  | r45  |
| 52_5 | r51  | r52  | r53  | r54  | r55  |

N / N-3

ULTRASOUND DIAGNOSIS APPARATUS AND ANALYZING APPARATUS

CROSS-REFERENCE TO RELATED APPLICATIONS

This application is based upon and claims the benefit of priority from Japanese Patent Application No. 2019-085456, filed on Apr. 26, 2019; the entire contents of which are incorporated herein by reference.

FIELD

Embodiments described herein relate generally to an ultrasound diagnosis apparatus and an analyzing apparatus.

BACKGROUND

An ultrasound diagnosis apparatus is configured to display, in a real-time manner, an ultrasound image represented by ultrasound image data generated, in a real-time manner, from an ultrasound scan and configured to display an ultrasound image represented by ultrasound image data obtained in a past ultrasound scan. Further, known functions include a Computer Aided Detection (CAD) function configured to automatically detect a characteristic site (a feature site) in a medical image generated by a medical image diagnosis apparatus. Further, an ultrasound diagnosis apparatus configured to detect a scan speed of an ultrasound probe by using a detector such as a magnetic sensor is also known. In this example, the scan speed is, for example, the speed (moving speed) of the ultrasound probe during moving of the ultrasound probe. The scan speed includes the speed of the ultrasound probe while the ultrasound probe is in a stopped state.

BRIEF DESCRIPTION OF THE DRAWINGS

FIG. 20 is a table illustrating an example of 25 correlation coefficients calculated in the second embodiment;

FIG. 21 is a table illustrating another example of 25 correlation coefficients calculated in the second embodiment;

FIG. 22 is a table illustrating yet another example of 25 correlation coefficients calculated in the second embodiment;

FIG. 23 is a table illustrating yet another example of 25 correlation coefficients calculated in the second embodiment;

DETAILED DESCRIPTION

An ultrasound diagnosis apparatus according to an embodiment includes processing circuitry. The processing circuitry is configured to generate moving speed information indicating a moving speed of an ultrasound probe, on the basis of a predetermined number of pieces of medical image data among a plurality of pieces of medical image data in a time series obtained from an ultrasound scan performed by the ultrasound probe. The processing circuitry is configured to cause a display to display the moving speed information.

Exemplary embodiments of an ultrasound diagnosis apparatus and a medical image processing apparatus will be explained below, with reference to the accompanying drawings. The description of each of the embodiments and the modification examples may similarly be applied to any other embodiment or modification example.

First Embodiment

Figure 1:
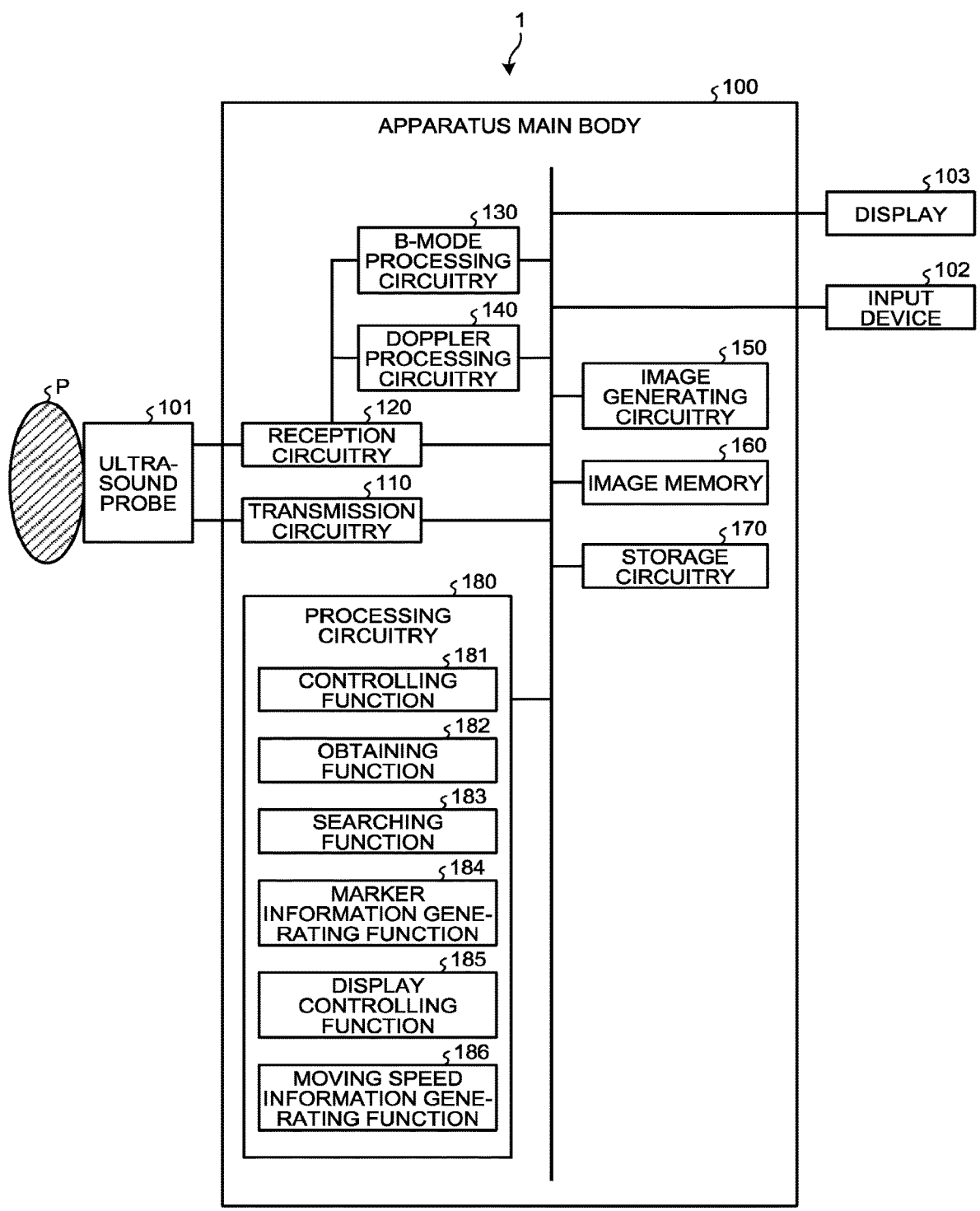
FIG. 1 is a diagram illustrating an exemplary configuration of an ultrasound diagnosis apparatus according to a first embodiment.

To begin with, an exemplary configuration of an ultrasound diagnosis apparatus 1 according to a first embodiment will be explained. FIG. 1 is a diagram illustrating the exemplary configuration of the ultrasound diagnosis apparatus according to the first embodiment. As illustrated in FIG. 1, the ultrasound diagnosis apparatus 1 according to the first embodiment includes an apparatus main body 100, an ultrasound probe 101, an input device 102, and a display 103.

For example, the ultrasound probe 101 includes a plurality of elements such as piezoelectric transducer elements. Each of the plurality of elements is configured to generate an ultrasound wave on the basis of a drive signal supplied thereto from transmission circuitry 110 included in the apparatus main body 100 (explained later). Further, the ultrasound probe 101 is configured to receive reflected waves from an examined subject (hereinafter "patient") P and to convert the received reflected waves into electric signals. Further, the ultrasound probe 101 includes, for example, a matching layer provided for the piezoelectric transducer elements, as well as a backing member or the like that prevents the ultrasound waves from propagating rearward from the piezoelectric transducer elements. In this situation, the ultrasound probe 101 is detachably connected to the apparatus main body 100.

When an ultrasound wave is transmitted from the ultrasound probe 101 to the patient P, the transmitted ultrasound wave is repeatedly reflected on a surface of discontinuity of acoustic impedances at a tissue in the body of the patient P and is received as a reflected wave by each of the plurality of elements included in the ultrasound probe 101. The amplitude of the received reflected wave is dependent on the difference between the acoustic impedances on the surface of discontinuity on which the ultrasound wave is reflected. When a transmitted ultrasound pulse is reflected on the surface of a moving blood flow, a cardiac wall, or the like, the reflected wave is, due to the Doppler effect, subject to a frequency shift, depending on a velocity component of the moving members with respect to the ultrasound wave transmission direction.

The ultrasound probe 101 can detachably be attached to the apparatus main body 100. When scanning a two-dimensional region inside the patient P (a two-dimensional scan), an operator connects, for example, a one-dimensional (1D) array probe in which the plurality of piezoelectric transducer elements are arranged in a row, to the apparatus main body 100 as the ultrasound probe 101. The 1D array probe may be a linear ultrasound probe, a convex ultrasound probe, a sector ultrasound probe, or the like. In contrast, when scanning a three-dimensional region inside the patient P (a three-dimensional scan), the operator connects, for example, a mechanical four-dimensional (4D) probe or a two-dimensional (2D) array probe to the apparatus main body 100, as the ultrasound probe 101. The mechanical 4D probe is capable of performing a two-dimensional scan by using the plurality of piezoelectric transducer elements arranged in a row like in the 1D array probe and is also capable of performing a three-dimensional scan by swinging the plurality of piezoelectric transducer elements at a predetermined angle (a swinging angle). Further, the 2D array probe is capable of performing a three-dimensional scan by using the plurality of piezoelectric transducer elements arranged in a matrix formation and is also capable of performing a two-dimensional scan by transmitting ultrasound waves in a converged manner.

For example, the input device 102 is realized by input means such as a mouse, a keyboard, a button, a panel switch, a touch command screen, a foot switch, a trackball, a joystick, and/or the like. The input device 102 is configured to receive various types of setting requests from the operator of the ultrasound diagnosis apparatus 1 and to transfer the received various types of setting requests to the apparatus main body 100. For example, the input device 102 is configured to receive an instruction (an execution instruction) to execute a CAD process from the operator of the ultrasound diagnosis apparatus 1 and to transmit the received execution instruction to processing circuitry 180 of the apparatus main body 100. Further, during a CAD process to automatically detect a characteristic site (a feature site) from an ultrasound image, the operator is also able to set, via the input device 102, a Region Of Interest (ROI), which is a search range for the feature site, in the ultrasound image.

For example, the display 103 is configured to display a Graphical User Interface (GUI) used by the operator of the ultrasound diagnosis apparatus 1 for inputting the various types of setting requests via the input device 102 and to display an ultrasound image represented by ultrasound image data generated by the apparatus main body 100, and the like. The display 103 is realized by using a liquid crystal monitor, a Cathode Ray Tube (CRT) monitor, or the like. The display 103 is an example of a display unit.

The apparatus main body 100 is configured to generate the ultrasound image data on the basis of reflected-wave signals transmitted thereto from the ultrasound probe 101. The apparatus main body 100 is capable of generating two-dimensional ultrasound image data on the basis of reflected-wave signals corresponding to the two-dimensional region of the patient P transmitted by the ultrasound probe 101. Further, the apparatus main body 100 is capable of generating three-dimensional ultrasound image data on the basis of reflected-wave signals corresponding to the three-dimensional region of the patient P transmitted by the ultrasound probe 101.

As illustrated in FIG. 1, the apparatus main body 100 includes the transmission circuitry 110, reception circuitry 120, B-mode processing circuitry 130, Doppler processing circuitry 140, image generating circuitry 150, an image memory 160, storage circuitry 170, and the processing circuitry 180. The transmission circuitry 110, the reception circuitry 120, the B-mode processing circuitry 130, the Doppler processing circuitry 140, the image generating circuitry 150, the image memory 160, the storage circuitry 170, and the processing circuitry 180 are connected so as to be able to communicate with one another.

Under control of the processing circuitry 180, the transmission circuitry 110 is configured to cause ultrasound waves to be transmitted from the ultrasound probe 101. The transmission circuitry 110 includes rate pulser generating circuitry, transmission delay circuitry, and a transmission pulser and is configured to supply the drive signal to the ultrasound probe 101. When a two-dimensional region inside the patient P is to be scanned, the transmission circuitry 110 causes an ultrasound beam for scanning the two-dimensional region to be transmitted from the ultrasound probe 101. Further, when a three-dimensional region inside the patient P is to be scanned, the transmission circuitry 110 causes an ultrasound beam for scanning the three-dimensional region to be transmitted from the ultrasound probe 101.

The rate pulser generating circuitry is configured to repeatedly generate a rate pulse for forming a transmission ultrasound wave (a transmission beam) at a predetermined rate frequency (i.e., a Pulse Repetition Frequency [PRF]). As a result of the rate pulse being routed through the transmission delay circuitry, voltage is applied to the transmission pulser with various transmission delay time periods. For example, the transmission delay circuitry is configured to apply a transmission delay time period that is required to converge the ultrasound waves generated by the ultrasound probe 101 into the form of a beam and to determine transmission directionality and that corresponds to each of the piezoelectric transducer elements, to each of the rate pulses generated by the rate pulser generating circuitry. The transmission pulser is configured to apply the drive signal (a drive pulse) to the ultrasound probe 101 with timing based on the rate pulses. In this situation, by varying the transmission delay time periods applied to the rate pulses, the transmission delay circuitry is able to arbitrarily adjust the transmission directions of the ultrasound waves transmitted from the surfaces of the piezoelectric transducer elements.

The drive pulse reaches the piezoelectric transducer elements in the ultrasound probe 101 from the transmission pulser via a cable and is subsequently converted from an electric signal into mechanical vibration at the piezoelectric transducer elements. Ultrasound waves generated by the mechanical vibration are transmitted to the inside of the patient's body. In this situation, the ultrasound waves having the transmission delay time periods varied in correspondence with the piezoelectric transducer elements are converged to be propagated in a predetermined direction.

Under control of the processing circuitry 180, the transmission circuitry 110 has a function that is able to instantly change transmission frequency, transmission drive voltage, and the like, for the purpose of executing a predetermined scan sequence. In particular, the function to change the transmission drive voltage is realized by using linear-amplifier-type transmission circuitry of which the value can be instantly switched or by using a mechanism configured to electrically switch between a plurality of power source units.

The reflected waves of the ultrasound waves transmitted by the ultrasound probe 101 reach the piezoelectric transducer elements inside the ultrasound probe 101 and are subsequently converted from the mechanical vibration to electric signals (reflected-wave signals) at the piezoelectric transducer elements, before being input to the reception circuitry 120. Under the control of the processing circuitry 180, the reception circuitry 120 is configured to generate reflected-wave data by performing various types of processes on the reflected-wave signals transmitted thereto from the ultrasound probe 101 and to output the generated reflected-wave data to the B-mode processing circuitry 130 and to the Doppler processing circuitry 140. For example, every time a reflected-wave signal is received, the reception circuitry 120 generates reflected-wave data from the received reflected-wave signal. The reception circuitry 120 is configured to generate two-dimensional reflected-wave data from two-dimensional reflected-wave signals transmitted thereto from the ultrasound probe 101. Further, the reception circuitry 120 is configured to generate three-dimensional reflected-wave data from three-dimensional reflected-wave signals transmitted thereto from the ultrasound probe 101.

The reception circuitry 120 includes a preamplifier, an Analog-to-Digital (A/D) converter, quadrature detecting circuitry, and the like. The pre-amplifier is configured to amplify the reflected-wave signals for each of the channels and to perform a gain adjusting process (a gain correction). The A/D converter is configured to convert the gain-corrected reflected-wave signals into digital signals by performing an A/D conversion on the gain-corrected reflected-wave signals. The quadrature detecting circuitry is configured to convert the digital signals into an In-phase signal (an I signal) and a Quadrature-phase signal (a Q signal) that are in a baseband. Further, the quadrature detecting circuitry is configured to output the I signal and the Q signal (IQ signals) to the B-mode processing circuitry 130 and to the Doppler processing circuitry 140, as the reflected-wave data.

Under the control of the processing circuitry 180, the B-mode processing circuitry 130 is configured to generate data (B-mode data) in which the signal intensity (amplitude intensity) at each sampling point is expressed with a degree of brightness, by performing a logarithmic amplification, an envelope detecting process, and a logarithmic compression, or the like on the reflected-wave data output from the reception circuitry 120. For example, every time reflected-wave data is received, the B-mode processing circuitry 130 generates B-mode data from the received reflected-wave data. The B-mode processing circuitry 130 is configured to output the generated B-mode data to the image generating circuitry 150. For example, the B-mode processing circuitry 130 is realized by using a processor.

Under the control of the processing circuitry 180, by performing a frequency analysis on the reflected-wave data output from the reception circuitry 120, the Doppler processing circuitry 140 is configured to extract motion information of moving members (blood flows, tissues, contrast agent echo components, and the like) based on the Doppler effect and to generate data (Doppler data) indicating the extracted motion information. For example, the Doppler processing circuitry 140 extracts an average velocity value, a dispersion value, a power value, and the like with respect to a large number of points as the motion information of the moving members and generates the Doppler data indicating the extracted motion information of the moving members. For example, every time reflected-wave data is received, the Doppler processing circuitry 140 generates Doppler data from the received reflected-wave data. The Doppler processing circuitry 140 is configured to output the generated Doppler data to the image generating circuitry 150. The Doppler processing circuitry 140 is realized by using a processor, for example.

The B-mode processing circuitry 130 and the Doppler processing circuitry 140 are capable of processing both the two-dimensional reflected-wave data and the three-dimensional reflected-wave data.

Under the control of the processing circuitry 180, the image generating circuitry 150 is configured to generate the ultrasound image data from the various types of data (the B-mode data and the Doppler data) output by the B-mode processing circuitry 130 and the Doppler processing circuitry 140. For example, every time the various types of data output from the B-mode processing circuitry 130 and the Doppler processing circuitry 140 are received, the image generating circuitry 150 generates ultrasound image data from the received various types of data. In other words, the image generating circuitry 150 is configured to generate, in a real-time manner, a plurality of pieces of ultrasound image data in a time series from the ultrasound scan. As described herein, in the present embodiment, the reception circuitry 120, the B-mode processing circuitry 130, the Doppler processing circuitry 140, and the image generating circuitry 150 are configured to acquire, in the real-time manner, the plurality of pieces of ultrasound image data in the time series. The reception circuitry 120, the B-mode processing circuitry 130, the Doppler processing circuitry 140, and the image generating circuitry 150 are examples of acquiring units. Further, the ultrasound image data is an example of the medical image data.

Further, the image generating circuitry 150 is configured to store the plurality of pieces of ultrasound image data in the time series generated in the real-time manner, into the image memory 160. In a specific example, every time a piece of ultrasound image data is generated, the image generating circuitry 150 stores the generated piece of ultrasound image data into the image memory 160. For example, among the plurality of pieces of ultrasound image data in the time series obtained from the ultrasound scan, the piece of ultrasound image data generated first will be referred to as "ultrasound image data in the first frame". Similarly, a piece of ultrasound image data generated in the N-th place in the sequence (where N is an integer of 1 or larger) will be referred to as "ultrasound image data in the N-th frame".

The image generating circuitry 150 is realized by using a processor. In this situation, the image generating circuitry 150 is configured to convert (by performing a scan convert process) a scanning line signal sequence from an ultrasound scan into a scanning line signal sequence in a video format used by, for example, television and generates display-purpose ultrasound image data. For example, the image generating circuitry 150 generates the display-purpose ultrasound image data by performing a coordinate transformation process in accordance with the ultrasound scanning mode used by the ultrasound probe 101. Further, as various types of image processing processes besides the scan convert process, the image generating circuitry 150 performs, for example, an image processing process (a smoothing process) to re-generate an average brightness value image, an image processing process (an edge enhancement process) that uses a differential filter inside an image, or the like, by using a plurality of image frames resulting from the scan convert process. Also, the image generating circuitry 150 combines text information of various types of parameters, scale graduations, body marks, and the like with the ultrasound image data.

Further, the image generating circuitry 150 is configured to generate three-dimensional B-mode image data by performing a coordinate transformation process on three-dimensional B-mode data generated by the B-mode processing circuitry 130. Further, the image generating circuitry 150 is configured to generate three-dimensional Doppler image data by performing a coordinate transformation process on three-dimensional Doppler data generated by the Doppler processing circuitry 140. In other words, the image generating circuitry 150 generates the "three-dimensional B-mode image data and three-dimensional Doppler image data" as "three-dimensional ultrasound image data (volume data)". Further, the image generating circuitry 150 is configured to perform any of various types of rendering processes on the volume data, to generate various types of two-dimensional image data for the purpose of displaying the volume data on the display 103.

The B-mode data and the Doppler data are each ultrasound image data before the scan convert process. The data generated by the image generating circuitry 150 is the display-purpose ultrasound image data after the scan convert process. The B-mode data and the Doppler data may be referred to as raw data.

The image memory 160 is a memory configured to store therein the various types of image data generated by the image generating circuitry 150. Further, the image memory 160 is also configured to store therein the data generated by the B-mode processing circuitry 130 and the Doppler processing circuitry 140. After a diagnosis process, for example, the operator is able to invoke any of the B-mode data and the Doppler data stored in the image memory 160. The invoked data can serve as display-purpose ultrasound image data after being routed through the image generating circuitry 150. For example, the image memory 160 is realized by using a semiconductor memory element such as a Random Access Memory (RAM) or a flash memory, or a hard disk, an optical disk, or the like.

The storage circuitry 170 is configured to store therein a control program for performing the ultrasound wave transmission and reception processes, image processing processes, and display processes, as well as diagnosis information (e.g., patients' IDs and observations of medical doctors) and various types of data such as diagnosis protocols, various types of body marks, and the like. Further, as necessary, the storage circuitry 170 may also be used for saving any of the data stored in the image memory 160 and the like. For example, the storage circuitry 170 is realized by using a semiconductor memory element such as a flash memory, or a hard disk, an optical disk, or the like. The image memory 160 and the storage circuitry 170 are examples of storage units.

The processing circuitry 180 is configured to control the entirety of processes performed by the ultrasound diagnosis apparatus 1. The processing circuitry 180 is realized by using a processor, for example. The processing circuitry 180 has processing functions, namely, a controlling function 181, an obtaining function 182, a searching function 183, a marker information generating function 184, a display controlling function 185, and a moving speed information generating function 186.

In this situation, for example, the processing functions of the processing circuitry 180 are stored in the storage circuitry 170 in the form of computer-executable programs. The processing functions of the constituent elements of the processing circuitry 180 illustrated in FIG. 1, namely, the controlling function 181, the obtaining function 182, the searching function 183, the marker information generating function 184, the display controlling function 185, and the moving speed information generating function 186, are stored in the storage circuitry 170 in the form of computer-executable programs. By reading the programs from the storage circuitry 170 and executing the read programs, the processing circuitry 180 realizes the functions corresponding to the programs. In other words, the processing circuitry 180 that has read the programs has the functions illustrated within the processing circuitry 180 in FIG. 1.

The term "processor" used in the above explanations denotes, for example, a Central Processing Unit (CPU), a Graphics Processing Unit (GPU), or circuitry such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The processors realize the functions by reading and executing the programs saved in storage circuitry 170. Instead of saving the programs in the storage circuitry 170, it is also acceptable to directly incorporate the programs into the circuitry of the processors. In that situation, the processors realize the functions by reading and executing the programs incorporated in the circuitry thereof. Further, the processors of the present embodiments do not each necessarily have to be configured as a single piece of circuitry. It is also acceptable to structure one processor by combining together two or more pieces of independent circuitry so as to realize the functions thereof. Further, two or more of the constituent elements illustrated in FIG. 1 may be integrated into one processor so as to realize the functions thereof. The same applies to the term "processor" used in the explanations below.

The controlling function 181 is configured to control processes performed by the transmission circuitry 110, the reception circuitry 120, the B-mode processing circuitry 130, the Doppler processing circuitry 140, and the image generating circuitry 150, on the basis of the various types of setting requests input by the operator via the input device 102 and the various types of data read from the storage circuitry 170.

The obtaining function 182 is configured to obtain the plurality of pieces of ultrasound image data in the time series, upon receipt of the instruction (the execution instruction) to execute a CAD process that is input by the operator via the input device 102. For example, every time a newly-generated piece of ultrasound image data is stored in the image memory 160 after the receiving of the execution instruction, the obtaining function 182 is configured to obtain the newly-generated piece of ultrasound image data from the image memory 160. For example, the plurality of pieces of ultrasound image data in the time series represent a group of data obtained from an ultrasound scan performed by the ultrasound probe 101. For example, the ultrasound scan may be performed while a scan region inside the patient P is moved as a result of the ultrasound probe 101 being moved by the operator along the body surface of the patient P or may be performed while the ultrasound probe 101 is stopped. In the explanations below, each of the plurality of pieces of ultrasound image data in a time series is, for example, B-mode image data.

The searching function 183 is configured to perform the CAD process to automatically detect a feature site in an ultrasound image represented by the ultrasound image data. For example, every time a newly-generated piece of ultrasound image data is obtained by the obtaining function 182, the searching function 183 performs the CAD process on the newly-generated piece of ultrasound image data. For example, the feature site may be a tumor in a mammary gland, but is not limited to this example. During the CAD process, by using a search window, training data, and a search algorithm, the searching function 183 is configured to search for the feature site in a search range (a ROI) set in the ultrasound image by the operator. For example, by moving the search window to a plurality of positions in the search range and analyzing, in each of the positions, image information in the search window with the use of the training data and the search algorithm, the searching function 183 is configured to calculate a probability of the image information in the search window corresponding to the feature site.

For example, the search window is a unit of a region in the search range to be compared with the training data. For example, the training data is image information serving as a specimen of the feature site. The search algorithm is an algorithm used for calculating the probability.

For example, the training data is image information of the feature site in ultrasound image data obtained in the past. In this situation, the training data may be information obtained through machine learning performed on the basis of the image information of the feature site in each of a plurality of pieces of ultrasound image data acquired in the past. Further, the search algorithm may be, for example, an algorithm that outputs a search result by searching for image information corresponding to the feature site in the ultrasound image subject to the processing, by using a network trained through machine learning.

Further, the searching function 183 is configured to detect a range enclosed in the search window as the feature site (a range of the feature site), when the calculated probability is equal to or higher than a predetermined threshold value. Further, for each piece of ultrasound image data corresponding to one frame, the searching function 183 stores the search result for the ultrasound image into the storage circuitry 170. For example, when having obtained the feature site as a result of searching for the feature site in an ultrasound image in any one frame, the searching function 183 stores position information indicating the position of the feature site into the storage circuitry 170 as a search result. In the present example, the position of the feature site is a position within the image space of the ultrasound image data.

Figure 2:
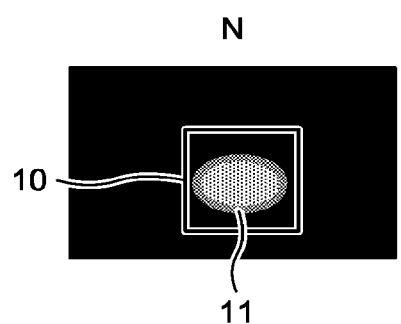
FIG. 2 is a drawing for explaining an example of a CAD process performed by a searching function according to the first embodiment.
Figure 3:
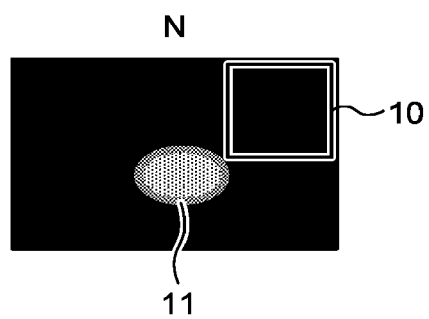
FIG. 3 is a drawing for explaining another example of the CAD process performed by the searching function according to the first embodiment.

With reference to FIGS. 2 and 3, the following sections will explain that the feature site detected by the searching function 183 may be either of two types of feature sites such as the feature site correctly detected and the feature site that is not actually the feature site but is erroneously detected. FIGS. 2 and 3 are drawings for explaining examples of the CAD process performed by the searching function 183 according to the first embodiment. In the following explanation, a piece of ultrasound image data newly generated by the image generating circuitry 150 will be referred to as ultrasound image data in an N-th frame.

FIG. 2 illustrates an example in which the searching function 183 has correctly detected the feature site. As illustrated in FIG. 2, for example, the searching function 183 detects, as the feature site, the range being enclosed in a search window 10 and containing an actual feature site 11, by performing a CAD process on the ultrasound image in the N-th frame. After that, the searching function 183 stores position information indicating the position of the feature site detected in the ultrasound image in the N-th frame, into the storage circuitry 170.

In contrast, FIG. 3 illustrates an example in which the searching function 183 has erroneously detected the feature site. As illustrated in FIG. 3, for example, the searching function 183 may, in some situations, detect a range being enclosed by the search window 10 and not containing the feature site 11 as the feature site, by performing a CAD process on the ultrasound image in the N-th frame. Detecting a feature site erroneously in this manner is called over-detection (a false positive).

Further, when being unable to detect the feature site as a result of searching for the feature site in an ultrasound image in any one frame, the searching function 183 is configured to store information indicating that it is impossible to detect the feature site, into the storage circuitry 170 as a search result.

As explained above, the searching function 183 is configured to set the search range in each of the plurality of ultrasound images respectively represented by the plurality of pieces of ultrasound image data obtained from the ultrasound scan and to search for the feature site in the search range set in each of the plurality of ultrasound images. The searching function 183 is an example of a searching unit. Alternatively, in place of the probabilities, the searching function 183 may be configured to calculate another index such as a degree of similarity indicating the level of similarity between the image information in each search window and the training data.

The marker information generating function 184 is configured to generate marker information indicating the detection result for the ultrasound image in each frame, on the basis of the plurality of search results for the ultrasound images in the plurality of frames.

An example of the plurality of search results for the plurality of frames used in a process performed by the marker information generating function 184 will be explained. When the most recent piece of ultrasound image data is the ultrasound image data in the N-th frame, for example, used as the plurality of search results are as many search results as "K+1", namely search results for ultrasound images in an (N−K)th frame to the N-th frame, where K is a natural number smaller than N. In the following sections, an example where K=2 will be explained.

The marker information generating function 184 obtains, from the storage circuitry 170, a search result for the ultrasound image in the (N−2)th frame, a search result for the ultrasound image in the (N−1)th frame, and a search result for the ultrasound image in the N-th frame (three search results).

After that, on the basis of the three search results, the marker information generating function 184 judges whether the feature site has been detected in the three pieces of ultrasound image data. In the present example, the three pieces of ultrasound image data are, for instance, the ultrasound image data in the (N−2)th frame, the ultrasound image data in the (N−1)th frame, and the ultrasound image data in the N-th frame. Further, when determining that the feature site has been detected in the three pieces of ultrasound image data, the marker information generating function 184 judges whether or not the positions of the three feature sites detected in the three pieces of ultrasound image data are sufficiently close to one another in the image space of the ultrasound image data. In this situation, the phrase "the positions of the three feature sites are sufficiently close to one another" means, for example, when the three features sites represent the same feature site, the three feature sites are present in a prescribed range in which the feature site can possibly be present in the three pieces of ultrasound image data. Further, when the positions of the three feature sites are determined to be sufficiently close to one another in the image space of the ultrasound image data, the marker information generating function 184 is configured to generate marker information indicating a rectangular marker expressing the range detected as the feature site.

On the contrary, when having determined that the feature site is not detected in all three of the pieces of ultrasound image data, the marker information generating function 184 is configured not to generate the marker information. Further, also when determining that the positions of the three feature sites detected in the three pieces of ultrasound image data are not sufficiently close to one another in the image space of the ultrasound image data, the marker information generating function 184 is configured not to generate the marker information.

Figure 4:
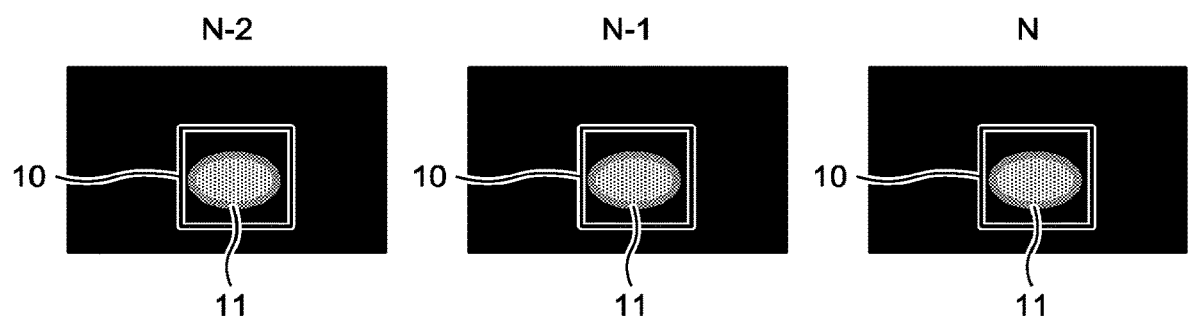
FIG. 4 is a drawing for explaining an example of processes performed by the searching function and a marker information generating function according to the first embodiment.
Figure 5:
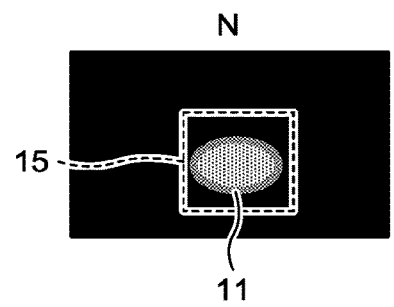
FIG. 5 is a drawing for explaining another example of the processes performed by the searching function and the marker information generating function according to the first embodiment.
Figure 6:
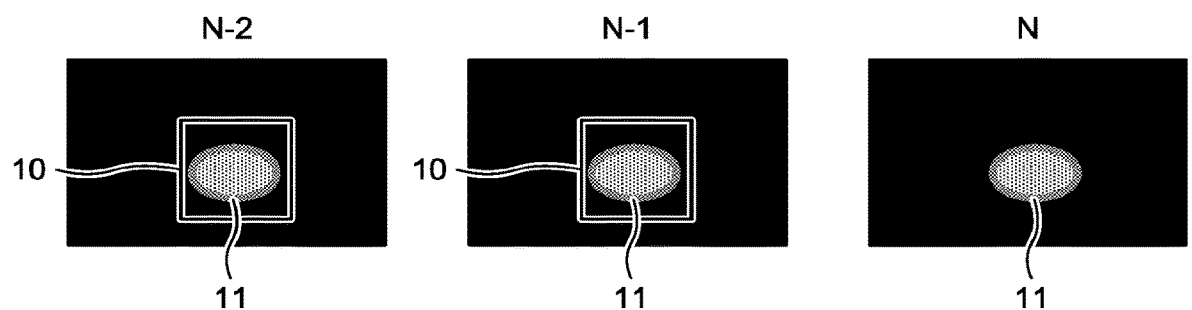
FIG. 6 is a drawing for explaining yet another example of the processes performed by the searching function and the marker information generating function according to the first embodiment.

With reference to FIGS. 4 to 6, specific examples of the processes performed by the searching function 183 and the marker information generating function 184 will be explained. FIGS. 4 to 6 are drawings for explaining the examples of processes performed by the searching function 183 and the marker information generating function 184 according to the first embodiment.

At first, an example will be explained in which, as illustrated in FIG. 4, the searching function 183 has detected a range being enclosed by the search window 10 and containing the actual feature site 11 as the feature site, from each of the three pieces of ultrasound image data. In this situation, for example, the marker information generating function 184 determines that the feature site has been detected in the three pieces of ultrasound image data. Further, the marker information generating function 184 judges whether or not the positions of the three feature sites detected in the three pieces of ultrasound image data are sufficiently close to one another in the image space. When the positions of the three feature sites are determined to be sufficiently close to one another in the image space, the marker information generating function 184 generates marker information indicating a rectangular marker 15 expressing the range detected as the feature site, as illustrated in FIG. 5. The marker information is information corresponding to the ultrasound image data in the N-th frame.

Next, another example will be explained in which, in the situation illustrated in FIG. 4, the searching function 183 has over-detected the feature site as illustrated in FIG. 3 explained above, instead of detecting the feature site correctly, from the ultrasound image data in the N-th frame. In this situation, for example, the marker information generating function 184 determines that the feature site has been detected in the three pieces of ultrasound image data. However, the marker information generating function 184 determines that the positions of the three features sites detected in the three pieces of ultrasound image data are not sufficiently close to one another in the image space. Accordingly, the marker information generating function 184 does not generate the marker information.

Next, yet another example will be explained in which, as illustrated in FIG. 6, the searching function 183 has detected a range being enclosed by the search window 10 and containing the actual feature site 11 as the feature site from each of two pieces of ultrasound image data (i.e., the ultrasound image data in the (N−2)th frame and the ultrasound image data in the (N−1)th frame) among the three pieces of ultrasound image data, but is unable to detect the feature site from the ultrasound image data in the N-th frame. In this situation, the marker information generating function 184 determines that the feature site has not been detected in all three of the pieces of ultrasound image data. Accordingly, the marker information generating function 184 does not generate the marker information.

In this manner, the marker information generating function 184 generates the marker information when the feature site has been detected in positions that are sufficiently close to one another, over a plurality of frames (three frames in the above example). For example, when the feature site 11 is a tumor in a mammary gland, because the tumor has a certain size, the tumor is rendered in ultrasound images over a plurality of frames. In contrast, in over-detection, a site different from the feature site 11 is erroneously detected, for example, and over-detection occurs abruptly in many situations. Thus, the possibility of having over-detection over a plurality of frames is low. Consequently, in the present embodiment, the marker information generating function 184 is configured to generate the marker information indicating that it is possible to detect the feature site, when the feature site has been detected in positions that are sufficiently close to one another over the plurality of frames. As a result, the present embodiment makes it possible to prevent the over-detection.

Further, when having generated the marker information corresponding to the ultrasound image data in the N-th frame, the marker information generating function 184 superimposes the marker 15 represented by the marker information, on the ultrasound image represented by the ultrasound image data in the N-th frame, as illustrated in FIG. 5. Further, the marker information generating function 184 stores ultrasound image data representing the ultrasound image having the marker 15 superimposed, into the image memory 160.

The display controlling function 185 is configured to cause the display 103 to display an ultrasound image represented by the display-purpose ultrasound image data stored in the image memory 160. The ultrasound image is an example of the medical image. The display controlling function 185 is an example of a display controlling unit.

For example, the display controlling function 185 is configured to cause the display 103 to display, in a real-time manner, the ultrasound image having the marker 15 superimposed. For example, every time a piece of ultrasound image data representing an ultrasound image having the marker 15 superimposed is stored into the image memory 160 by the marker information generating function 184, the display controlling function 185 obtains the piece of ultrasound image data presenting the ultrasound image having the marker 15 superimposed, from the image memory 160. Further, every time a piece of ultrasound image data representing an ultrasound image having the marker 15 superimposed is obtained, the display controlling function 185 causes the display 103 to display the ultrasound image having the marker 15 superimposed.

Figure 7:
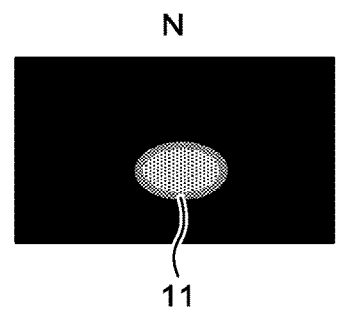
FIG. 7 is a drawing illustrating a display example according to the first embodiment.

Further, the display controlling function 185 is configured to cause the display 103 to also display, in a real-time manner, the ultrasound images having no marker 15 superimposed. For example, every time the marker information generating function 184 determines that the feature site has not been detected in all three of the pieces of ultrasound image data described above, the display controlling function 185 causes the display 103 to display the ultrasound image represented by the ultrasound image data in the N-th frame, as illustrated in FIG. 7. Further, every time the marker information generating function 184 determines that the positions of the three feature sites detected in the three pieces of ultrasound image data are not sufficiently close to one another in the image space, the display controlling function 185 causes the display 103 to display the ultrasound image represented by the ultrasound image data in the N-th frame illustrated in FIG. 7. FIG. 7 is a drawing illustrating the display example according to the first embodiment.

In the present example, as explained above, the marker information generating function 184 is configured to judge whether or not the feature site has been detected in positions sufficiently close to one another over a plurality of frames (the three frames in the above example). Further, when the feature site has been detected in positions sufficiently close to one another over the plurality of frames, the marker information generating function 184 is configured to generate the marker information indicating that it is possible to detect the feature site. Further, the display controlling function 185 is configured to cause the display 103 to display the ultrasound image having the marker 15 superimposed, the marker 15 being represented by the marker information. As a result, it is possible to prevent the over-detection and to detect the feature site with an excellent level of precision.

However, the level of precision for detecting the feature site is dependent on the scan speed of the ultrasound probe 101. In this situation, the scan speed denotes, for example, the speed (the moving speed) of the ultrasound probe 101 while the ultrasound probe 101 is moving along the body surface of the patient P according to an operation performed by the operator. In this situation, the scan speed includes the speed of the ultrasound probe 101 while the ultrasound probe 101 is in a stopped state. For example, when the moving speed of the ultrasound probe 101 is relatively high, the moving amount (the moving distance) of the ultrasound probe 101 over a plurality of frames (the three frames in the above example) is large. In that situation, there is a possibility that the actual feature site 11 may be detected only in some of the plurality of frames, while the actual feature site 11 is not detected in the other frames. In that situation, the display 103 does not display the marker 15 indicating that the feature site 11 such as a tumor has been detected. Accordingly, when the moving speed of the ultrasound probe 101 is relatively high, detection sensitivity for the feature site 11 may be degraded.

On the contrary, for example, when the moving speed of the ultrasound probe 101 is relatively low, the moving amount of the ultrasound probe 101 over the plurality of frames is small. In that situation, there is a possibility, for example, that a site different from the feature site 11 may erroneously be over-detected over two or more frames. As a result, because the over-detection occurs over the two or more frames, the display 103 displays the marker 15 indicating that the site different from the feature site 11 has been detected as the feature site. Consequently, when the moving speed of the ultrasound probe 101 is relatively low, the occurrence of over-detection increases.

For this reason, it is desirable to enable the operator to understand whether or not the moving speed of the ultrasound probe 101 is appropriate.

In this regard, it may be possible to detect the moving speed of the ultrasound probe 101 by using a detector such as a magnetic sensor. However, using a detector would incur costs such as an expense to purchase the detector or the like. Further, if a detector was attached to the ultrasound probe 101, it would be difficult to manipulate the ultrasound probe 101. Furthermore, it is not possible to use a magnetic sensor when the patient P is using a pacemaker.

To cope with these circumstances, the ultrasound diagnosis apparatus 1 according to the first embodiment performs various types of processes explained below, to enable the operator to understand whether or not the moving speed of the ultrasound probe 101 is appropriate, without using a detector.

The moving speed information generating function 186 according to the first embodiment is configured to generate moving speed information indicating the moving speed of the ultrasound probe 101, on the basis of a predetermined number of pieces of ultrasound image data among a plurality of pieces of ultrasound image data obtained from an ultrasound scan. For example, on the basis of two pieces of ultrasound image data, the moving speed information generating function 186 generates, as the moving speed information, information indicating an enclosure which represents a search range and of which the display mode varies in accordance with the moving speed of the ultrasound probe 101. The moving speed information generating function 186 is an example of a generating unit.

Figure 8:
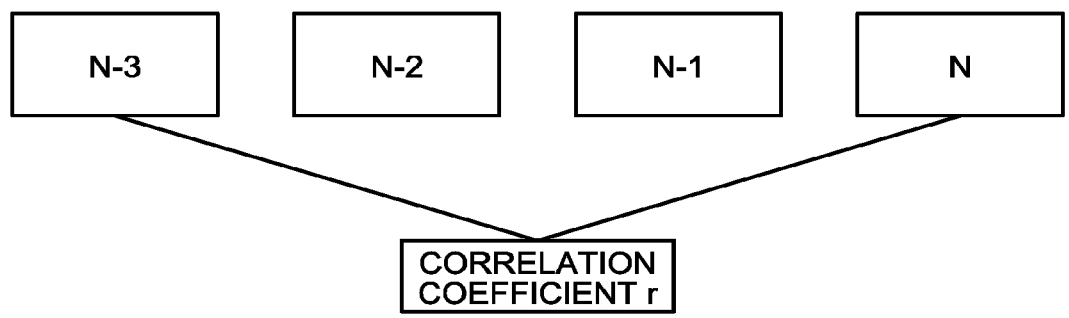
FIG. 8 is a drawing for explaining an example of a process performed by a moving speed information generating function according to the first embodiment.

FIG. 8 is a drawing for explaining an example of a process performed by the moving speed information generating function 186 according to the first embodiment.

For example, every time the obtaining function 182 obtains a newly-generated piece of ultrasound image data (the ultrasound image data in the N-th frame), the moving speed information generating function 186 calculates a correlation coefficient r to be used in the process explained later, by using the ultrasound image data in the (N−3)th frame and the ultrasound image data in the N-th frame, as illustrated in FIG. 8.

Figure 9:
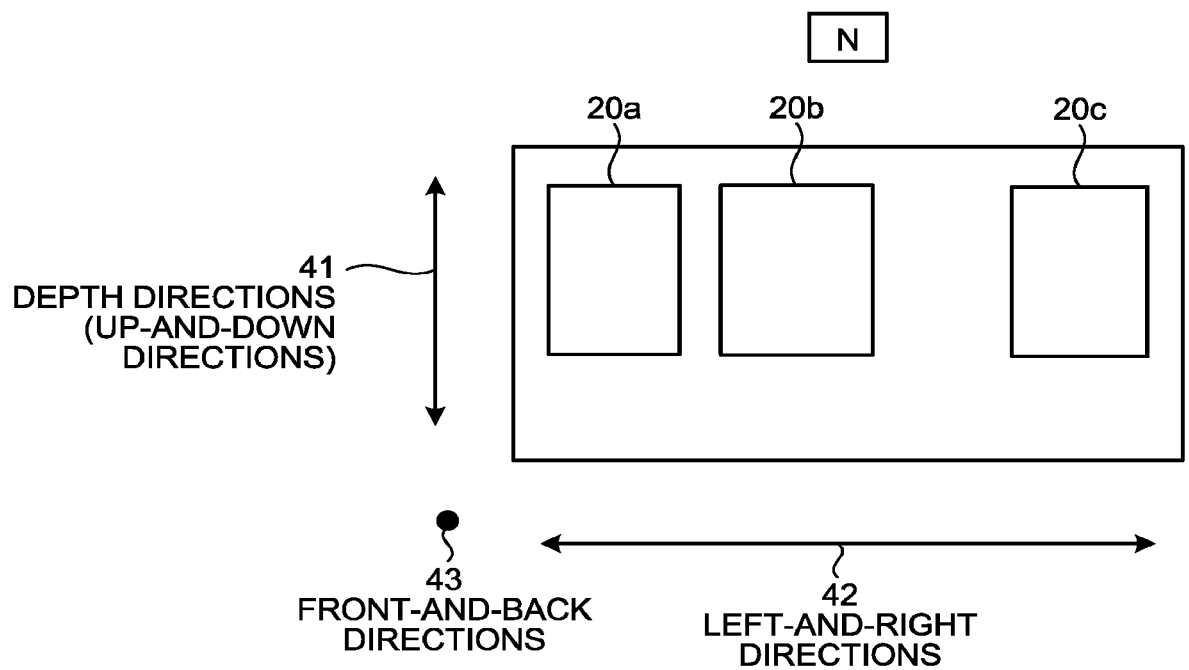
FIG. 9 is a drawing for explaining an example of a method for calculating a correlation coefficient according to the first embodiment.
Figure 10:
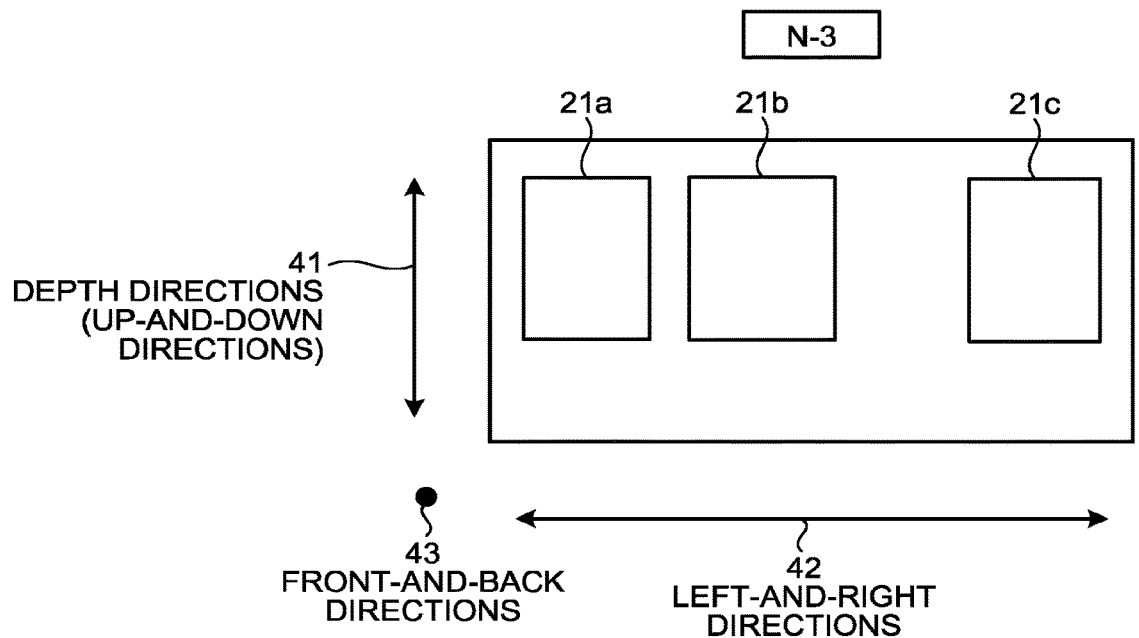
FIG. 10 is another drawing for explaining the example of the method for calculating the correlation coefficient according to the first embodiment.
Figure 11:
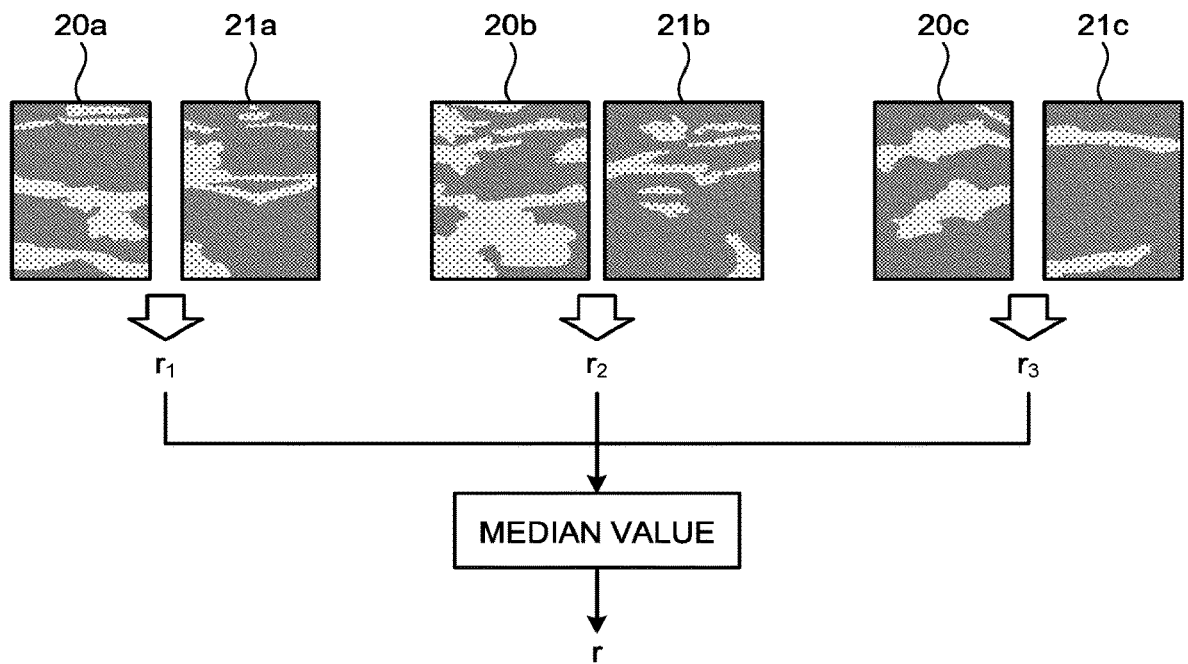
FIG. 11 is yet another drawing for explaining the example of the method for calculating the correlation coefficient according to the first embodiment.

A specific example of a method for calculating the correlation coefficient r will be explained, with reference to FIGS. 9 to 11. FIGS. 9 to 11 are drawings for explaining the example of the method for calculating the correlation coefficient r according to the first embodiment.

FIG. 9 illustrates an example of the ultrasound image represented by the ultrasound image data in the N-th frame. FIG. 10 illustrates an example of the ultrasound image represented by the ultrasound image data in the (N−3)th frame. In FIGS. 9 and 10, the top section of the ultrasound image corresponds to a shallower section in terms of the depth directions (up-and-down directions; the directions indicated with a bidirectional arrow 41) of the skin or the like of the patient P. Further, in FIGS. 9 and 10, the bottom section of the ultrasound image corresponds to a section deeper, in terms of the depth directions, than the ribs of the patient P.

For example, it is assumed that the image information in the shallower section such as the skin rendered in the ultrasound image is uniform and has almost no change. Further, for example, because ultrasound waves are strongly reflected by the ribs, the reflected waves of the ultrasound waves coming from the section deeper than the ribs are weakened. The ultrasound image thus has a shadow (an acoustic shadow) in which the section deeper than the ribs appears dark. For this reason, it is assumed that the image information of the section deeper than the ribs is uniform and has almost no change.

Further, among the plurality of piezoelectric transducer elements included in the ultrasound probe 101, one or more piezoelectric transducer elements may not be in contact with the body surface of the patient P in some situations. In other words, there may be some piezoelectric transducer elements that are off the body surface. In that situation, of the entire region of the ultrasound image, the section based on reflected-wave signals from the piezoelectric transducer elements that are not in contact with the body surface of the patient P appear dark uniformly in the depth direction.

Accordingly, to generate high-precision moving speed information about the moving speed of the ultrasound probe 101, the moving speed information generating function 186 cuts out three regions 20a, 20b, and 20c, as illustrated in FIG. 9, instead of one region. More specifically, the moving speed information generating function 186 cuts out the three regions 20a, 20b, and 20c along left-and-right directions (the directions indicated with a bidirectional arrow 42), from a section excluding the shallower section and the deeper section from the ultrasound image in the N-th frame. For the same reason, the moving speed information generating function 186 cuts out, as illustrated in FIG. 10, three regions 21a, 21b, and 21c along the left-and-right directions from a section excluding the shallower section and the deeper section from the ultrasound image in the (N−3)th frame. As illustrated in FIGS. 9 and 10, the three regions 20a, 20b, and 20c and the three regions 21a, 21b, and 21c each have a rectangular shape. The number of regions cut out from the ultrasound images in the frames does not necessarily have to be three and may be any value other than 3. Further, the shape of each of the regions cut out from the ultrasound images in the frames does not necessarily have to be rectangular and may be a shape other than rectangles. Further, the positions of the regions cut out from the ultrasound images in the frames do not necessarily have to be the positions illustrated in FIGS. 9 and 10 and may be other positions besides those illustrated in FIGS. 9 and 10.

A purpose of the first embodiment is to enable the operator to understand whether or not the moving speed of the ultrasound probe 101 is appropriate while the ultrasound probe 101 is moving in a direction corresponding to either of the front-and-back directions (the directions indicated with a bidirectional arrow 43: the directions penetrating the ultrasound image) orthogonal to the up-and-down directions and to the left-and-right directions, and not in a direction corresponding to one of the up-and-down directions and the left-and-right directions of the ultrasound image. Accordingly, from the two pieces of ultrasound image data, the moving speed information generating function 186 cuts out the regions 20a and 21a in mutually the same position in the image space of the ultrasound image data. In this situation, the two pieces of ultrasound image data are the ultrasound image data in the (N−3)th frame and the ultrasound image data in the N-th frame. Further, from the two pieces of ultrasound image data, the moving speed information generating function 186 cuts out the regions 20b and 21b in mutually the same position in the image space of the ultrasound image data. Also, from the two pieces of ultrasound image data, the moving speed information generating function 186 cuts out the regions 20c and 21c in mutually the same position in the image space of the ultrasound image data.

After that, as illustrated in FIG. 11, the moving speed information generating function 186 calculates a correlation coefficient r1 between the region 20a and the region 21a. Further, the moving speed information generating function 186 calculates a correlation coefficient r2 between the region 20b and the region 21b. Also, the moving speed information generating function 186 calculates a correlation coefficient r3 between the region 20c and the region 21c.

Subsequently, as illustrated in FIG. 11, the moving speed information generating function 186 calculates the median value of the correlation coefficients r1, r2, and r3 and determines the calculated median value to be the correlation coefficient r used for judging the moving speed of the ultrasound probe 101.

Alternatively, the moving speed information generating function 186 may calculate the average value of the correlation coefficients r1, r2, and r3, to determine the calculated average value as the correlation coefficient r.

The median value and the average value of the correlation coefficients r1, r2, and r3 are examples of statistical values of the correlation coefficients r1, r2, and r3.

In this situation, it is considered that the lower the moving speed of the ultrasound probe 101 is, the larger is the correlation coefficient r; and the higher the moving speed of the ultrasound probe 101 is, the smaller is the correlation coefficient r. An example of the reasons will be explained. For example, the higher the moving speed of the ultrasound probe 101 is, the distance in real space is longer between the scan region of the ultrasound scan in the (N−3)th frame and the scan region of the ultrasound scan in the N-th frame. The longer the distance in real space is, the larger is the difference between the form of a structure of the patient P rendered in the ultrasound image in the (N−3)th frame and the form of the structure of the patient P rendered in the ultrasound image in the N-th frame. For this reason, it is considered that the higher the moving speed of the ultrasound probe 101 is, the smaller is the correlation coefficient r.

Conversely, the lower the moving speed of the ultrasound probe 101 is, the distance in real space is shorter between the scan region of the ultrasound scan in the (N−3)th frame and the scan region of the ultrasound scan in the N-th frame. The shorter the distance in real space is, the smaller is the difference between the form of a structure of the patient P rendered in the ultrasound image in the (N−3)th frame and the form of the structure of the patient P rendered in the ultrasound image in the N-th frame. For this reason, it is considered that the lower the moving speed of the ultrasound probe 101 is, the larger is the correlation coefficient r.

As explained herein, the correlation coefficient r exhibits values corresponding to moving speeds of the ultrasound probe 101.

Figure 12:
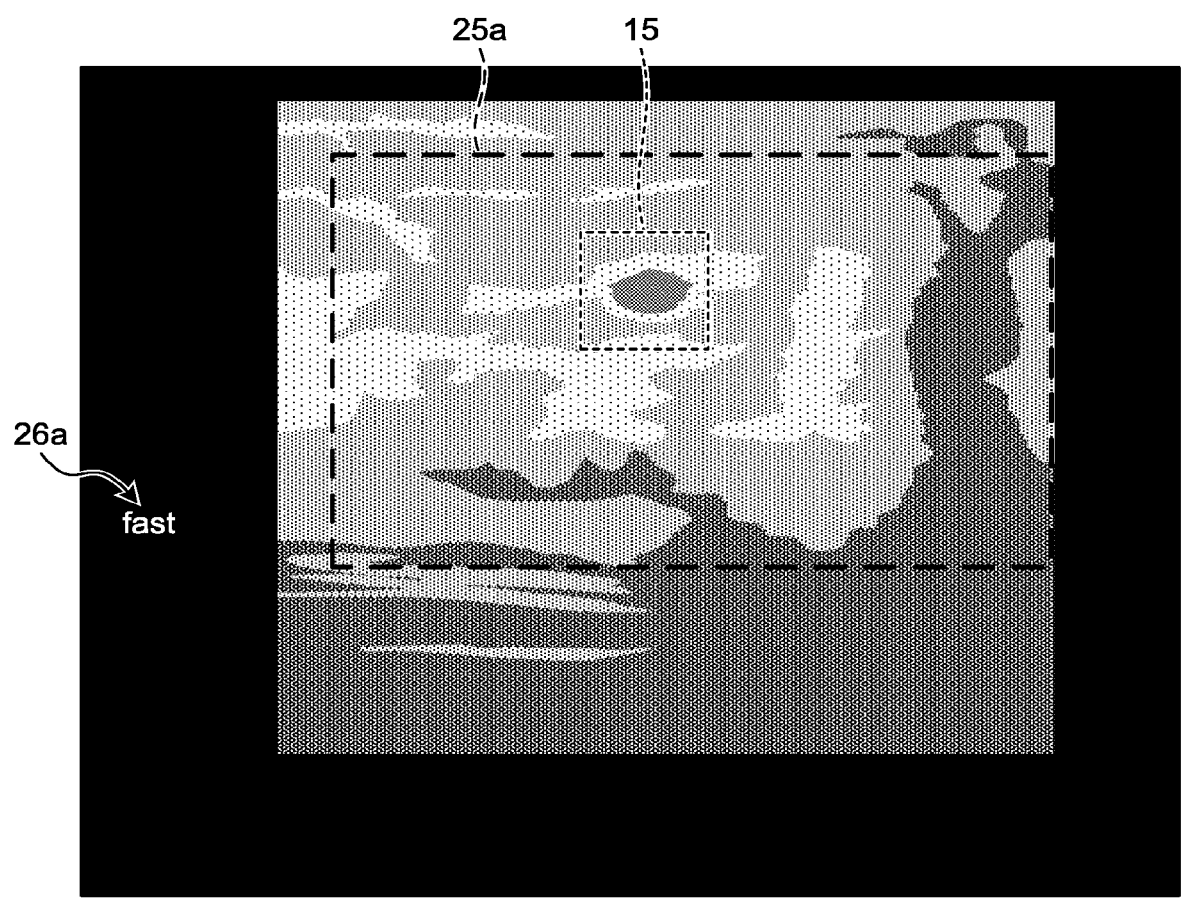
FIG. 12 is a drawing for explaining an example of processes performed by the ultrasound diagnosis apparatus according to the first embodiment.
Figure 13:
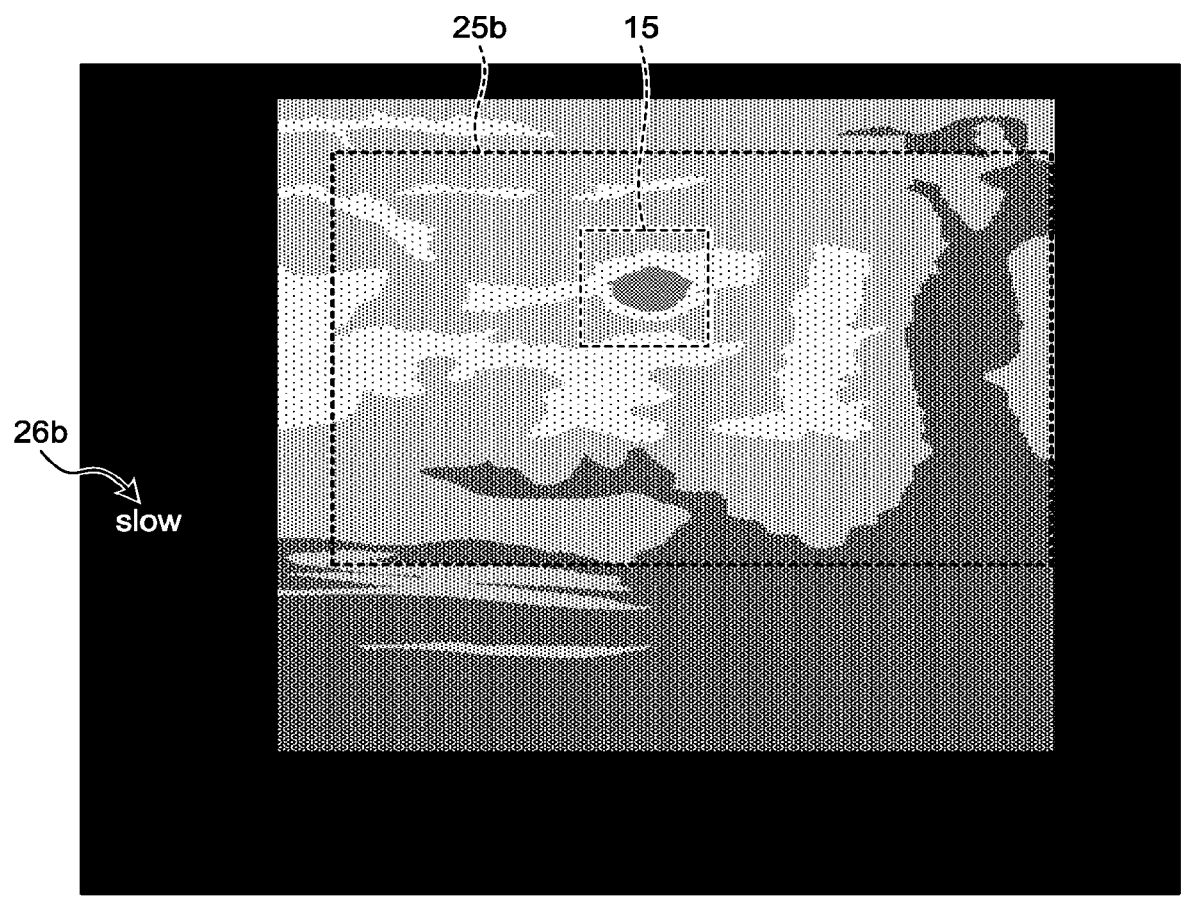
FIG. 13 is a drawing for explaining another example of the processes performed by the ultrasound diagnosis apparatus according to the first embodiment.
Figure 14:
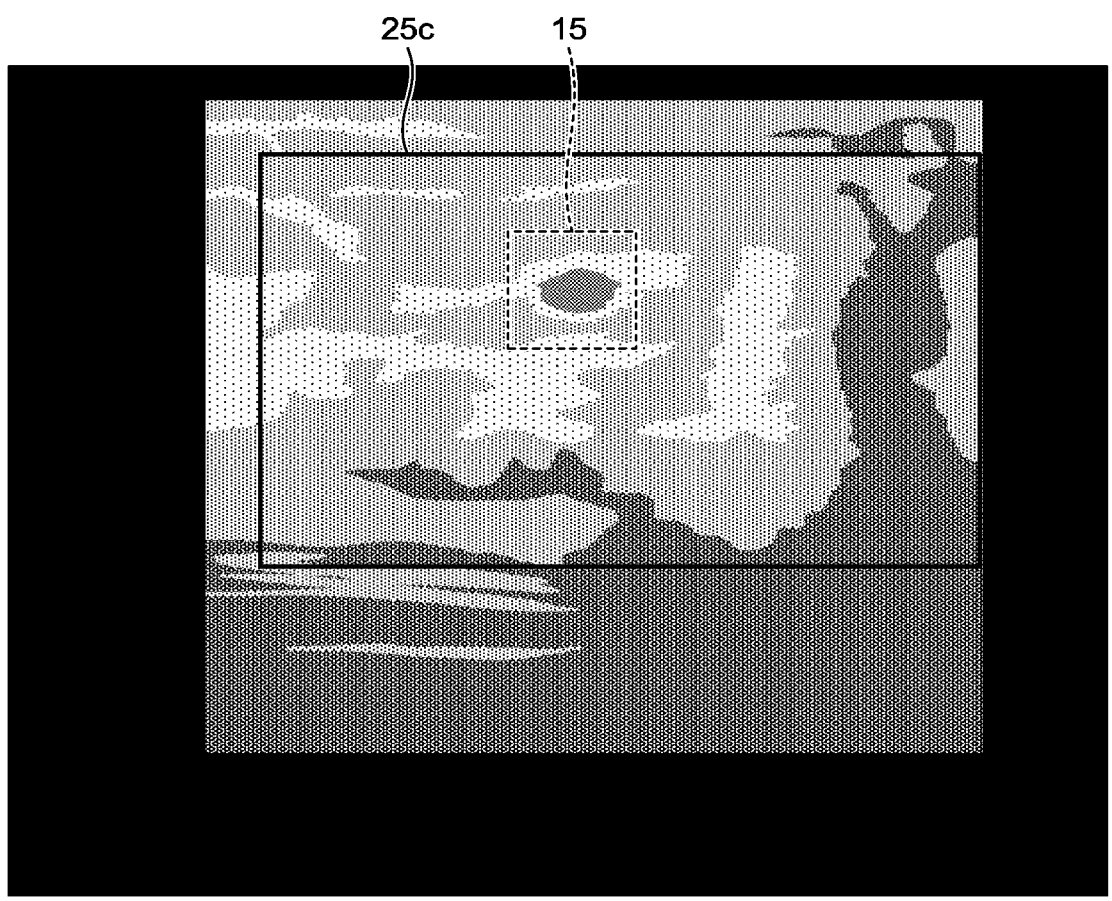
FIG. 14 is a drawing for explaining yet another example of the processes performed by the ultrasound diagnosis apparatus according to the first embodiment.

Further, the moving speed information generating function 186 is configured to generate, as the moving speed information, information indicating an enclosure which represents a search range and of which the display mode varies in accordance with the correlation coefficient r. Every time a correlation coefficient r is calculated, the moving speed information generating function 186 generates information indicating the enclosure. FIGS. 12 to 14 are drawings for explaining examples of processes performed by the ultrasound diagnosis apparatus 1 according to the first embodiment.

When the moving speed of the ultrasound probe 101 is relatively high, the moving speed information generating function 186 generates, as illustrated in FIG. 12, information indicating a red enclosure 25a as moving speed information. The red enclosure 25a indicates that the moving speed of the ultrasound probe 101 is relatively high. For example, when the correlation coefficient r is equal to or larger than 0.0 but is smaller than a threshold value T1, because the moving speed of the ultrasound probe 101 is relatively high, the moving speed information generating function 186 generates the information indicating the red enclosure 25a. Although the enclosure 25a is drawn with a broken line in the example of FIG. 12 to indicate that the enclosure 25a is in red, the enclosure 25a is formed with a solid line.

Further, when the correlation coefficient r is equal to or larger than 0 but is smaller than the threshold value T1, the moving speed information generating function 186 generates a character string "fast" 26a indicating that the moving speed of the ultrasound probe 101 is relatively high, as moving speed information.

In contrast, when the moving speed of the ultrasound probe 101 is relatively low, the moving speed information generating function 186 generates, as illustrated in FIG. 13, information indicating a yellow enclosure 25b as moving speed information. The yellow enclosure 25b indicates that the moving speed of the ultrasound probe 101 is relatively low. For example, when the correlation coefficient r is larger than a threshold value T2, because the moving speed of the ultrasound probe 101 is relatively low, the moving speed information generating function 186 generates the information indicating the yellow enclosure 25b. The threshold value T2 is larger than the threshold value T1. Although the enclosure 25b is drawn with a broken line in the example of FIG. 13 to indicate that the enclosure 25b is in yellow, the enclosure 25b is formed with a solid line.

Further, when the correlation coefficient r is larger than the threshold value T2, the moving speed information generating function 186 generates a character string "slow" 26b indicating that the moving speed of the ultrasound probe 101 is relatively low, as moving speed information.

In another example, when the moving speed of the ultrasound probe 101 is not too high, not too low, and is appropriate, the moving speed information generating function 186 generates, as illustrated in FIG. 14, information indicating an enclosure 25c in a predetermined default color (e.g., black or green) as moving speed information. The enclosure 25c in the default color indicates that the moving speed of the ultrasound probe 101 is appropriate. For example, when the correlation coefficient r is in the range from the threshold value T1 to the threshold value T2, inclusive, because the moving speed of the ultrasound probe 101 is appropriate, the moving speed information generating function 186 generates the information indicating the enclosure 25c in the default color.

As explained herein, the moving speed information generating function 186 is configured to generate the moving speed information so that the display mode thereof is varied in accordance with the moving speed of the ultrasound probe 101 corresponding to the correlation coefficient r. Further, the moving speed information generating function 186 is configured to generate the moving speed information in a real-time manner.

The display controlling function 185 is configured to cause the display 103 to display the moving speed information in a real-time manner. For example, every time moving speed information is generated by the moving speed information generating function 186, the display controlling function 185 causes the display 103 to display the generated moving speed information.

For example, when the information indicating the enclosure 25a in FIG. 12 explained above is generated, the display controlling function 185 causes, as illustrated in FIG. 12, the red enclosure 25a to be displayed over the ultrasound image in the N-th frame displayed on the display 103. Further, for example, when the character string "fast" 26a illustrated in FIG. 12 explained above is generated, the display controlling function 185 causes, as illustrated in FIG. 12, the character string "fast" 26a to be displayed to the left side of the ultrasound image in the N-th frame displayed on the display 103.

In another example, when the information indicating the enclosure 25b in FIG. 13 explained above is generated, the display controlling function 185 causes, as illustrated in FIG. 13, the yellow enclosure 25b to be displayed over the ultrasound image in the N-th frame displayed on the display 103. Further, for example, when the character string "slow" 26b illustrated in FIG. 13 explained above is generated, the display controlling function 185 causes, as illustrated in FIG. 13, the character string "slow" 26b to be displayed to the left side of the ultrasound image in the N-th frame displayed on the display 103.

In yet another example, when the information indicating the enclosure 25c in FIG. 14 explained above is generated, the display controlling function 185 causes, as illustrated in FIG. 14, the enclosure 25c in the default color to be displayed over the ultrasound image in the N-th frame displayed on the display 103.

In this situation, to enable the operator to understand the moving speed of an ultrasound probe, it may be possible to cause a display to display a value of the moving speed of the ultrasound probe detected by a magnetic sensor or the like, in a display region different from the display region in which the ultrasound image is displayed. Further, in elastography, for example, stress is applied by the operator to the surface of a tissue of the patient's body by applying and releasing pressure to and from the tissue while shaking the ultrasound probe, so as to obtain information about strain of the tissue inside the patient's body caused by the stress. Accordingly, it may also be possible to cause a display to display the information about the strain of the tissue as information related to motion of the ultrasound probe, in a display region different from a display region in which the ultrasound image is displayed.

In those situations, however, the value of the moving speed of the ultrasound probe and the information about the strain would not be displayed over the ultrasound image. For this reason, to understand the value of the moving speed of the ultrasound probe or the information about the strain, the operator would need to take his/her line of sight away from the ultrasound image.

In contrast, the ultrasound diagnosis apparatus 1 according to the first embodiment is configured to display the enclosures 25a, 25b, and 25c over the ultrasound images. Consequently, by using the ultrasound diagnosis apparatus 1 according to the first embodiment, the operator is able to understand whether or not the moving speed of the ultrasound probe 101 is appropriate, while viewing the ultrasound image.

Further, the ultrasound diagnosis apparatus 1 according to the first embodiment is capable of enabling the operator to understand the moving speed of the ultrasound probe 101, without using a detector such as a magnetic sensor that detects the moving speed of the ultrasound probe 101.

Figure 15:
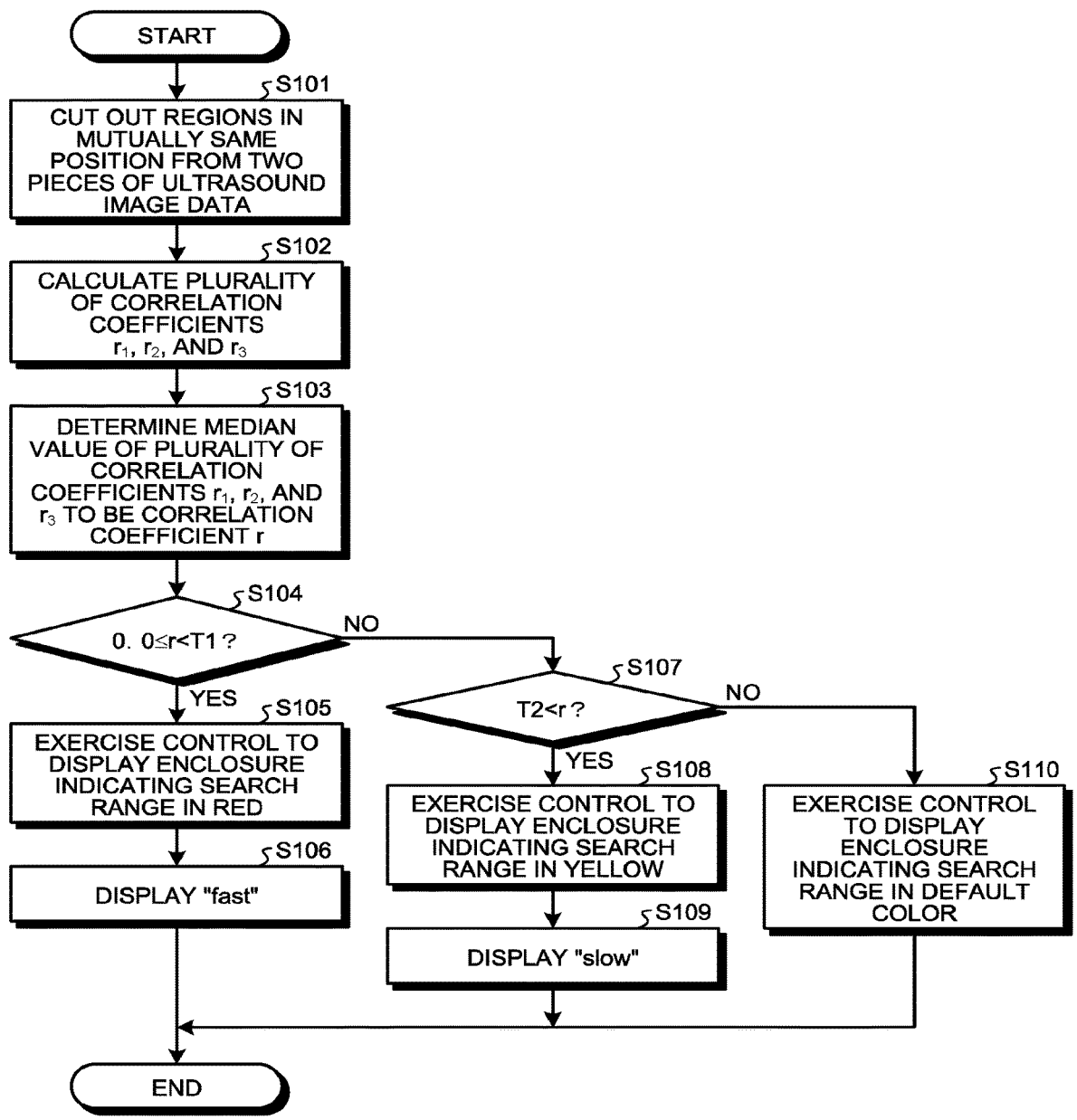
FIG. 15 is a flowchart for explaining an example of a flow in a process performed by the ultrasound diagnosis apparatus according to the first embodiment.

FIG. 15 is a flowchart for explaining an example of a flow in a process performed by the ultrasound diagnosis apparatus according to the first embodiment. The process in FIG. 15 is performed every time the obtaining function 182 obtains a piece of ultrasound image data (the ultrasound image data in the N-th frame) newly generated by the image generating circuitry 150.

As illustrated in FIG. 15, the moving speed information generating function 186 cuts out regions in mutually the same position in the image space, from the ultrasound image data in the N-th frame and the ultrasound image data in the (N−3)th frame (step S101). For example, at step S101, the moving speed information generating function 186 cuts out the regions 20a and 21a in mutually the same position, the regions 20b and 21b in mutually the same position, and the regions 20c and 21c in mutually the same position, from the ultrasound image data in the N-th frame and the ultrasound image data in the (N−3)th frame. Thus, the moving speed information generating function 186 is configured to cut out the plurality of regions in the plurality of mutually-the-same positions in the image space, from the two pieces of ultrasound image data.

Further, the moving speed information generating function 186 calculates the correlation coefficient r1 between the region 20a and the region 21a, the correlation coefficient r2 between the region 20b and the region 21b, and the correlation coefficient r3 between the region 20c and the region 21c (step S102). Thus, the moving speed information generating function 186 is configured to calculate the plurality of correlation coefficients in the plurality of mutually-the-same positions.

After that, the moving speed information generating function 186 calculates the median value of the correlation coefficients r1, r2, and r3 and determines the calculated median value to be the correlation coefficient r used for judging the moving speed of the ultrasound probe 101 (step S103).

Further, the moving speed information generating function 186 judges whether or not the correlation coefficient r is equal to or larger than 0.0 but is smaller than the threshold value T1 (step S104). When it is determined that the correlation coefficient r is equal to or larger than 0.0 but is smaller than the threshold value T1 (step S104: Yes), the following process is performed at step S105. For example, at step S105, the moving speed information generating function 186 generates the information indicating the red enclosure 25a, so that the display controlling function 185 causes the red enclosure 25a to be displayed over the ultrasound image in the N-th frame displayed on the display 103.

Further, at step S106, the moving speed information generating function 186 generates the character string "fast" 26a as moving speed information, so that the display controlling function 185 causes the character string "fast" 26a to be displayed to the left side of the ultrasound image in the N-th frame displayed on the display 103. After that, the moving speed information generating function 186 ends the process presented in FIG. 15.

On the contrary, when the correlation coefficient r is determined to be larger than the threshold value T1 (step S104: No), the moving speed information generating function 186 judges whether or not the correlation coefficient r is larger than the threshold value T2 (step S107).

When the correlation coefficient r is determined to be larger than the threshold value T2 (step S107: Yes), the following process is performed at step S108. For example, at step S108, the moving speed information generating function 186 generates the information indicating the yellow enclosure 25b, so that the display controlling function 185 causes the yellow enclosure 25b to be displayed over the ultrasound image in the N-th frame displayed on the display 103.

Further, at step S109, the moving speed information generating function 186 generates the character string "slow" 26b as moving speed information, so that the display controlling function 185 causes the character string "slow" 26b to be displayed to the left side of the ultrasound image in the N-th frame displayed on the display 103. After that, the moving speed information generating function 186 ends the process presented in FIG. 15.

On the contrary, when the correlation coefficient r is determined to be equal to or smaller than the threshold value T2 (step S107: No), in other words, when the correlation coefficient r is in the range from the threshold value T1 to the threshold value T2, inclusive, the following process is performed at step S110. For example, at step S110, the moving speed information generating function 186 generates the information indicating the enclosure 25c in the default color, so that the display controlling function 185 causes the enclosure 25c in the default color to be displayed over the ultrasound image in the N-th frame displayed on the display 103. After that, the moving speed information generating function 186 ends the process presented in FIG. 15.

In other words, at steps S104 through S110, the moving speed information generating function 186 is configured to calculate the moving speed information on the basis of the median value (the correlation coefficient r) of the calculated plurality of correlation coefficients r1, r2, and r3.

The ultrasound diagnosis apparatus 1 according to the first embodiment has thus been explained. By using the ultrasound diagnosis apparatus 1 according to the first embodiment, it is possible, as explained above, to enable the operator to understand the moving speed of the ultrasound probe 101, without using a detector such as a magnetic sensor that detects the moving speed of the ultrasound probe 101.

First Modification Example of First Embodiment

In the first embodiment, the example was explained in which the moving speed information generating function 186 generates the moving speed information by using the ultrasound image data in the (N−3)th frame and the ultrasound image data in the N-th frame; however, the moving speed information generating function 186 may select two pieces of ultrasound image data to be used for generating the moving speed information, in accordance with framerates of the ultrasound image data. Accordingly, this embodiment will be explained as a first modification example of the first embodiment.

In the first modification example of the first embodiment, the moving speed information generating function 186 is configured to select two pieces of ultrasound image data so that, regardless of the framerate value, the time difference between the two pieces of ultrasound image data (the time difference between the two frames) to be used for generating the moving speed information is constant. In this situation, the time difference between the two pieces of ultrasound image data is, for example, the distance between the two pieces of ultrasound image data in the time direction. For example, in the first modification example of the first embodiment, the moving speed information generating function 186 is configured to select two pieces of ultrasound image data in such a manner that the higher the framerate of the ultrasound image data is, the larger is the difference between the frame numbers of the two pieces of ultrasound image data to be used for generating the moving speed information. The reason is that, if the difference between the frame numbers of the two pieces of ultrasound image data were constant, because the time difference would decrease as the framerate increases, the correlation coefficient r between the two pieces of ultrasound image data would have a tendency of increasing, which might degrade the level of precision of the moving speed information generated from the correlation coefficient r. Similarly, in the first modification example of the first embodiment, the moving speed information generating function 186 is configured to select two pieces of ultrasound image data in such a manner that the lower the framerate of the ultrasound image data is, the smaller is the difference between the frame numbers of the two pieces of ultrasound image data to be used for generating the moving speed information.

For example, in the first modification example of the first embodiment, when the framerate is f1, the moving speed information generating function 186 selects, as the two pieces of ultrasound image data to be used for generating the moving speed information, ultrasound image data in an (N−L)th frame and the ultrasound image data in the N-th frame, where L is a positive integer smaller than N. Further, the moving speed information generating function 186 generates moving speed information by using the ultrasound image data in the (N−L)th frame and the ultrasound image data in the N-th frame.

In another example, when the framerate is f2, which is higher than f1, the moving speed information generating function 186 selects, as the two pieces of ultrasound image data to be used for generating the moving speed information, ultrasound image data in an (N−(L+2))th frame and the ultrasound image data in the N-th frame. Further, the moving speed information generating function 186 generates moving speed information by using the ultrasound image data in the (N−(L+2))th frame and the ultrasound image data in the N-th frame.

The first modification example of the first embodiment has thus been explained. As explained above, in the first modification example of the first embodiment, the moving speed information generating function 186 is configured to select the two pieces of ultrasound image data to be used for generating the moving speed information in accordance with the frame rates of the ultrasound image data. Further, the moving speed information generating function 186 is configured to generate the moving speed information on the basis of the two selected pieces of ultrasound image data. As a result, according to the first modification example of the first embodiment, it is possible to generate the moving speed information with an excellent level of precision. Further, according to the first modification example of the first embodiment, it is possible, similarly to the first embodiment, to enable the operator to understand the moving speed of the ultrasound probe 101, without using a detector such as a magnetic sensor that detects the moving speed of the ultrasound probe 101.

Second Modification Example of First Embodiment

A purpose of the first embodiment was to enable the operator to understand whether or not the moving speed is appropriate, while the ultrasound probe 101 is moving in a direction corresponding to either of the front-and-back directions explained above. Accordingly, in the first embodiment, the example was explained in which the moving speed information generating function 186 cuts out the regions in mutually the same position from the two pieces of ultrasound image data. However, the purpose may be to enable the operator to understand whether or not the moving speed is appropriate while the ultrasound probe 101 is moving in a direction corresponding to one of the up-and-down directions and the left-and-right directions explained above. Further, for this purpose, the moving speed information generating function 186 may cut out regions in mutually-different positions from two pieces of ultrasound image data. Accordingly, this embodiment will be explained as a second modification example of the first embodiment. In the explanations of the second modification example of the first embodiment, a focus will be placed on differences from the first embodiment, and the explanations of some of the configurations and the processes that are the same as those in the first embodiment may be omitted.

Figure 16:
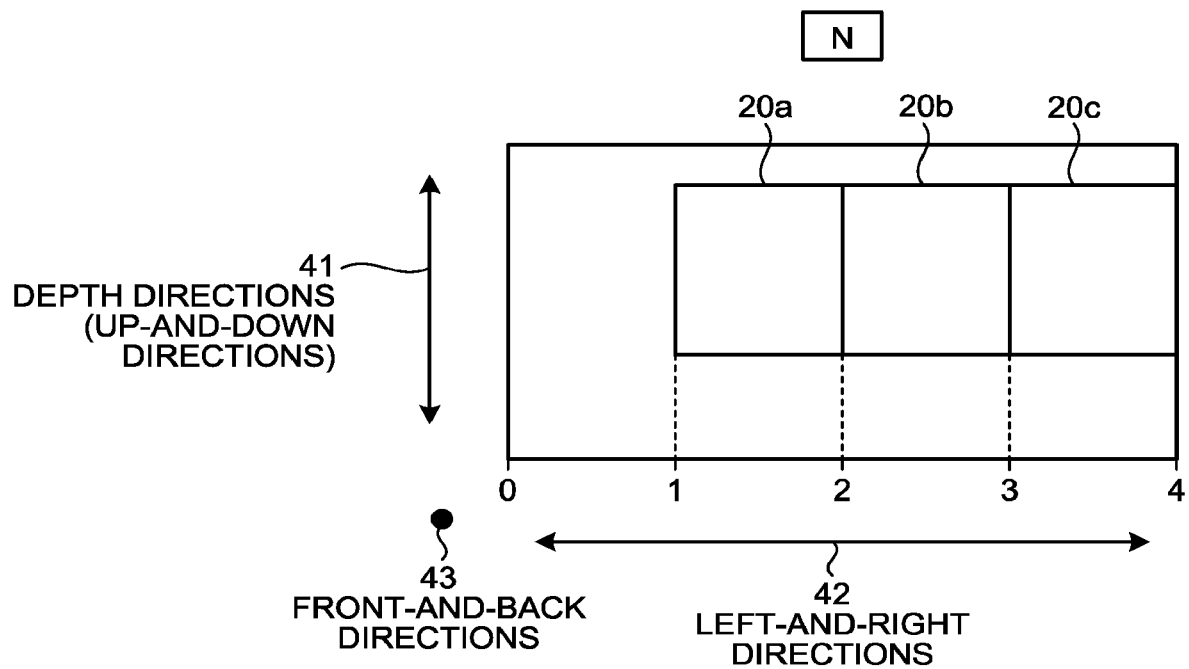
FIG. 16 is a drawing for explaining an example of a method for calculating a correlation coefficient according to a second modification example of the first embodiment.
Figure 17:
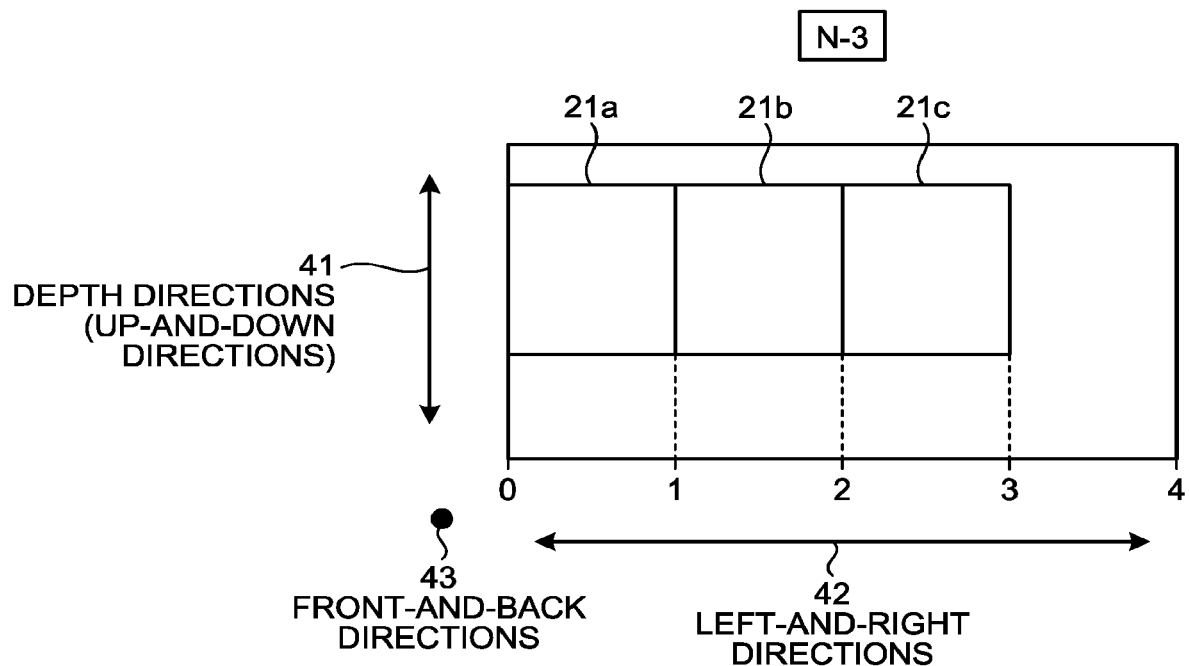
FIG. 17 is another drawing for explaining the example of the method for calculating the correlation coefficient according to the second modification example of the first embodiment.

In the following sections, an example will be explained in which a purpose is to enable the operator to understand whether or not the moving speed in a direction corresponding to either of the left-and-right directions is appropriate. A specific example of a method for calculating the correlation coefficient r in the second modification example of the first embodiment will be explained, with reference to FIGS. 16 and 17. FIGS. 16 and 17 are drawings for explaining the example of the method for calculating the correlation coefficient r according to the second modification example of the first embodiment.

FIG. 16 illustrates an example of the ultrasound image represented by the ultrasound image data in the N-th frame. FIG. 17 illustrates an example of the ultrasound image represented by the ultrasound image data in the (N−3)th frame. As illustrated in FIGS. 16 and 17, the width of the visual field (the length in the left-and-right directions) of the ultrasound image data in the N-th frame and the (N−3)th frame is 4 cm.

As illustrated in FIG. 16, the moving speed information generating function 186 cuts out a region 20a having a width that spans from the position 1 cm away from the left end (the position at 0 cm) to the right, to the position 2 cm away from the left end to the right, in the ultrasound image in the N-th frame. Further, the moving speed information generating function 186 cuts out a region 20b having a width that spans from the position 2 cm away from the left end to the right, to the position 3 cm away from the left end to the right, in the ultrasound image in the N-th frame. Also, the moving speed information generating function 186 cuts out a region 20c having a width that spans from the position 3 cm away from the left end to the right, to the position 4 cm away from the left end to the right, in the ultrasound image in the N-th frame.

Further, as illustrated in FIG. 17, the moving speed information generating function 186 cuts out a region 21a having a width that spans from the position at the left end (the position at 0 cm), to the position 1 cm away from the left end to the right, in the ultrasound image in the (N−3)th frame. Further, the moving speed information generating function 186 cuts out a region 21b having a width that spans from the position 1 cm away from the left end to the right, to the position 2 cm away from the left end to the right, in the ultrasound image in the (N−3)th frame. Also, the moving speed information generating function 186 cuts out a region 21c having a width that spans from the position 2 cm away from the left end to the right in the ultrasound image in the (N−3)th frame, to the position 3 cm away from the left end to the right in the same ultrasound image.

As explained herein, the moving speed information generating function 186 is configured to cut out the two regions 20a and 21a in the mutually-different positions. In addition, the moving speed information generating function 186 is configured to cut out the regions 20b and 21b in the mutually-different positions. Also, the moving speed information generating function 186 is configured to cut out the regions 20c and 21c in the mutually-different positions. In the present modification example, to enable the operator to understand whether or not the moving speed of the ultrasound probe 101 is appropriate in a direction corresponding to either of the left-and-right directions, the positions of the regions 20a and 21a are arranged to be out of alignment in the left-and-right directions. For the same reason, the positions of the regions 20b and 21b are also arranged to be out of alignment in the left-and-right directions. Also, the positions of the regions 20c and 21c are also arranged to be out of alignment in the left-and-right directions.

In other words, in the second modification example of the first embodiment, the moving speed information generating function 186 cuts out the plurality of regions that are out of alignment in the left-and-right directions, from the two pieces of ultrasound image data. When the purpose is to enable the operator to understand whether or not the moving speed is appropriate in a direction corresponding to either of the up-and-down directions, the moving speed information generating function 186 shall be configured to cut out a plurality of regions that are out of alignment in the up-and-down directions, from the two pieces of ultrasound image data.

After that, similarly to the first embodiment, the moving speed information generating function 186 calculates a correlation coefficient r1 between the region 20a and the region 21a, a correlation coefficient r2 between the region 20b and the region 21b, and a correlation coefficient r3 between the region 20c and the region 21c.

Further, similarly to the first embodiment, the moving speed information generating function 186 determines the largest value among the correlation coefficients r1, r2, and r3 as a correlation coefficient r to be used for estimating the moving speed of the ultrasound probe 101. Alternatively, the moving speed information generating function 186 may determine the median value or the average value of the correlation coefficients r1, r2, and r3 as a correlation coefficient r to be used for estimating the moving speed of the ultrasound probe 101. Further, similarly to the first embodiment, the moving speed information generating function 186 generates moving speed information by using the correlation coefficient r.

The second modification example of the first embodiment has thus been explained. As explained above, in the second modification example of the first embodiment, the moving speed information generating function 186 is configured to cut out the plurality of regions that are out of alignment in the left-and-right directions from the two pieces of ultrasound image data. As a result, according to the second modification example of the first embodiment, it is possible to generate the moving speed information about the ultrasound probe 101 moving in a direction corresponding to either of the left-and-right directions, with an excellent level of precision. Further, according to the second modification example of the first embodiment, it is possible, similarly to the first embodiment, to enable the operator to understand the moving speed of the ultrasound probe 101, without using a detector such as a magnetic sensor that detects the moving speed of the ultrasound probe 101.

Second Embodiment

Next, the ultrasound diagnosis apparatus 1 according to a second embodiment will be explained. In the explanations of the second embodiment, a focus will be placed on differences from the first embodiment, and the explanations of some of the configurations and the processes that are the same as those in the first embodiment may be omitted.

Figure 18:
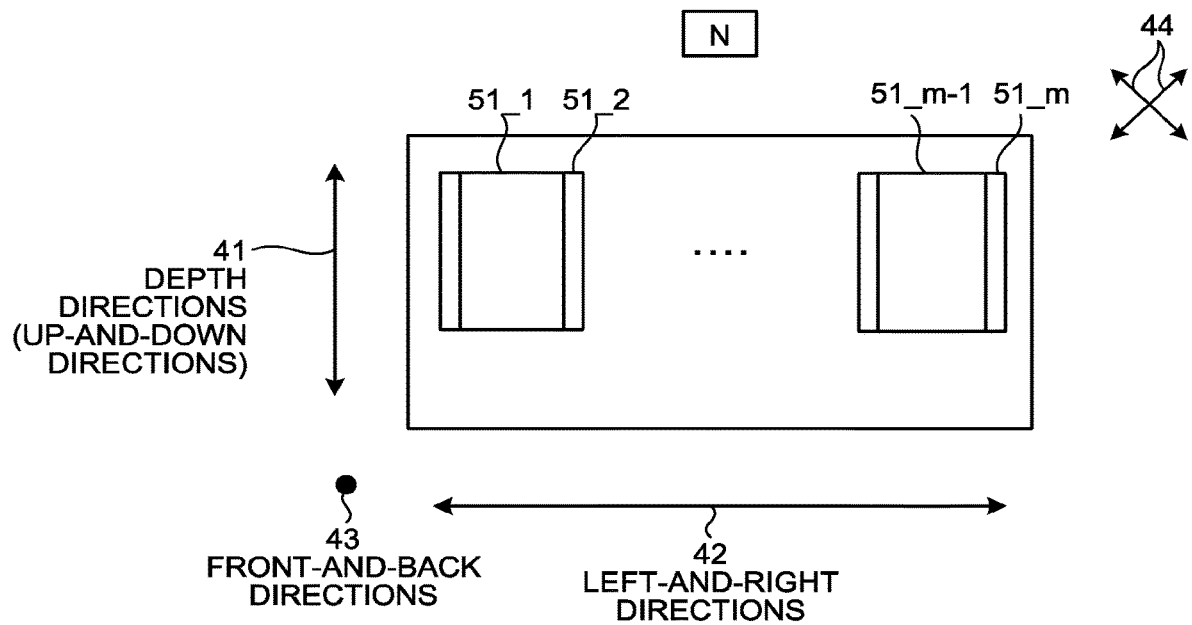
FIG. 18 is a drawing for explaining an example of a process performed by a moving speed information generating function according to a second embodiment.
Figure 19:
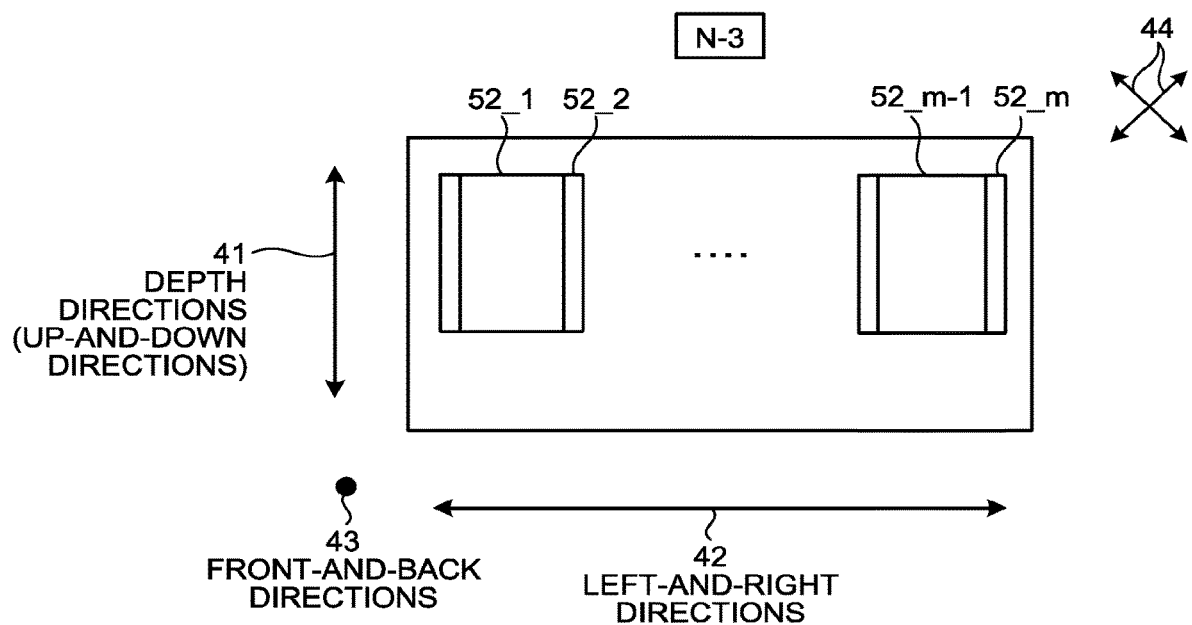
FIG. 19 is another drawing for explaining the example of the process performed by the moving speed information generating function according to the second embodiment.

FIGS. 18 and 19 are drawings for explaining an example of a process performed by the moving speed information generating function 186 according to the second embodiment. Every time the obtaining function 182 obtains a newly-generated piece of ultrasound image data (the ultrasound image data in the N-th frame), the moving speed information generating function 186 cuts out a plurality of regions 51_1 to 51_m (where m is a natural number) from the ultrasound image in the N-th frame, as illustrated in FIG. 18. In the example in FIG. 18, the position of the region 51_k+1 is slightly out of alignment, to the right, with the position of the region 51_k (where k=1, 2, . . . , or m−1). Further, a part of the region 51_k is overlaid on (overlaps with) a part of the region 51_k+1. Each of the regions 51_1 to 51_m is an example of the first region.

Further, as illustrated in FIG. 19, the moving speed information generating function 186 cuts out a plurality of regions 52_1 to 52_m from the ultrasound image in the (N−3)th frame. In the example in FIG. 19, the position of the region 52_k+1 is slightly out of alignment, to the right, with the position of the region 52_k. Further, a part of the region 52_k is overlaid on a part of the region 52_k+1. Each of the regions 52_1 to 52_m is an example of the second region.

In this situation, the positions of the plurality of regions 51_1 to 51_m in the image space of the ultrasound image data may be the same as or may be different from the positions of the plurality of regions 52_1 to 52_m in the image space of the ultrasound image data, respectively. In the following sections, an example will be explained in which the positions of the plurality of regions 51_1 to 51_m are the same as the positions of the plurality of regions 52_1 to 52_m, respectively.

Alternatively, the region 51_k and the region 51_k+1 may be positioned adjacent to each other, instead of overlapping with each other. Similarly, the region 52_k and the region 52_k+1 may be positioned adjacent to each other, instead of overlapping with each other.

Further, the moving speed information generating function 186 identifies all the possible combinations each made up of one of the plurality of regions 51_1 to 51_m and one of the plurality of regions 52_1 to 52_m. In the following sections, each of the plurality of regions 51_1 to 51_m will simply be referred to as a region 51, whereas each of the plurality of regions 52_1 to 52_m may simply be referred to as a region 52. In the following sections, an example in which "m" is 5 will be explained. In this situation, there are five regions as the plurality of regions 51, and also, there are five regions as the plurality of regions 52. In the present example, the moving speed information generating function 186 identifies 25 (5×5) combinations (sets). Further, for each of the combinations, the moving speed information generating function 186 calculates a correlation coefficient between the one region 51 and the one region 52 in the combination. In other words, for each of all the possible combinations made up of one region 51 and one region 52, the moving speed information generating function 186 calculates a correlation coefficient. For example, when having identified the 25 combinations, the moving speed information generating function 186 calculates 25 correlation coefficients.

Figures 20, 21:
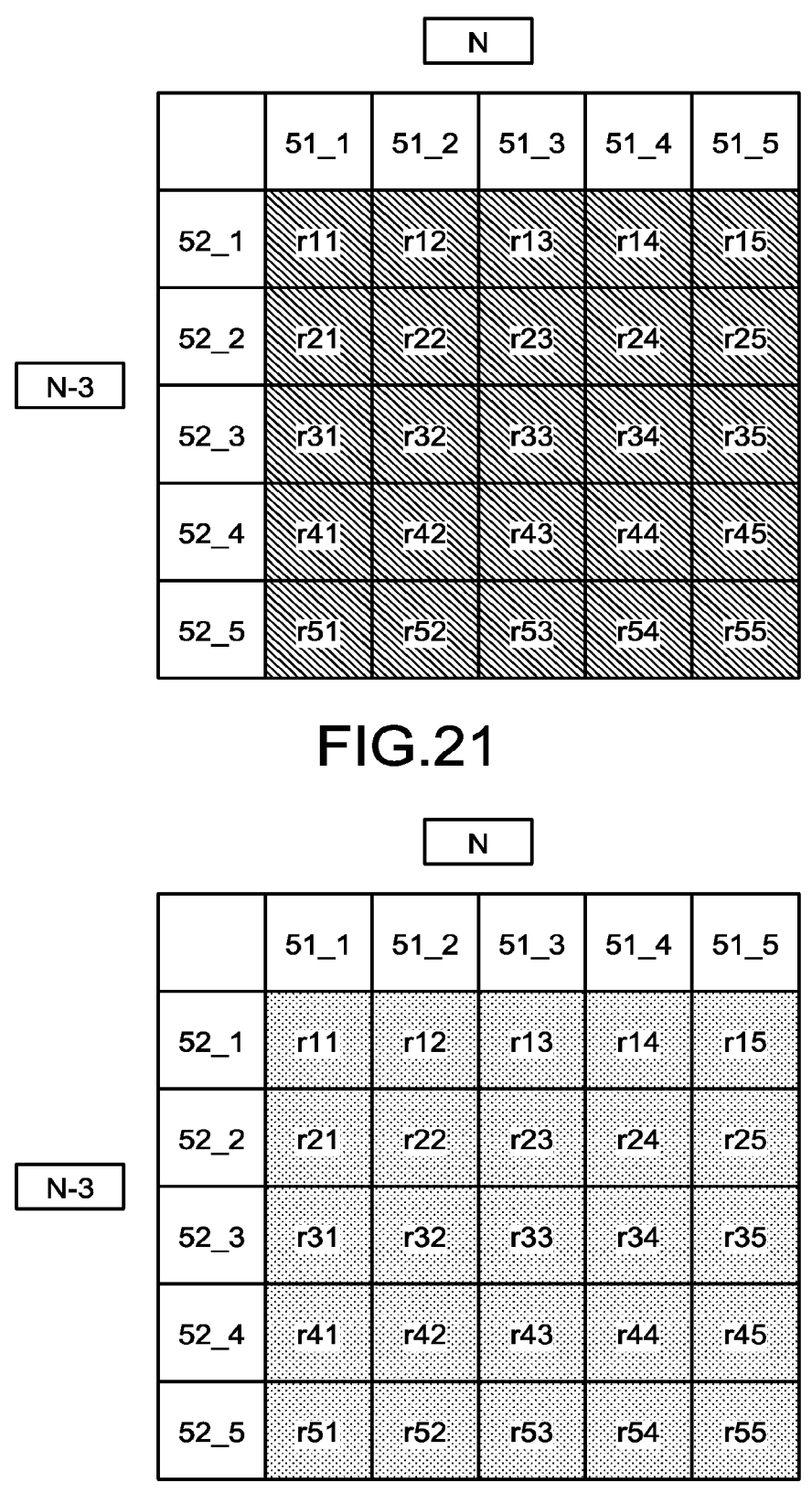

FIG. 20 is a table illustrating an example of the 25 correlation coefficients calculated in the second embodiment. In FIG. 20, "rsu" denotes a correlation coefficient between a region 52_s and a region 51_u (where s=1, 2, ..., or 5; and u=1, 2, ..., or 5). For example, "r23" denotes a correlation coefficient between a region 52_2 and a region 51_3. The same applies to FIGS. 21 to 23 and 25 explained later.

Further, with respect to each of the 25 correlation coefficients, the moving speed information generating function 186 judges whether or not the correlation coefficient is equal to or larger than 0.0 but is smaller than the threshold value T1. Further, the moving speed information generating function 186 judges whether or not any of the correlation coefficients determined to be equal to or larger than the threshold value T1 is larger than the threshold value T2.

In FIG. 20, the correlation coefficients larger than the threshold value T2 are indicated with diagonal hatching. In the example in FIG. 20, the 25 correlation coefficients are all larger than the threshold value T2. Accordingly, in the example in FIG. 20, it is considered that the ultrasound probe 101 is either stopped or moving relatively slowly in a direction corresponding to either of the front-and-back directions (the directions indicated with the bidirectional arrow 43 in FIGS. 18 and 19).

Accordingly, the moving speed information generating function 186 generates the information indicating the yellow enclosure 25b. Further, the moving speed information generating function 186 generates the character string "slow" 26b. As explained herein, the moving speed information generating function 186 is configured to generate the moving speed information on the basis of the 25 (plurality of) calculated correlation coefficients. Further, the display controlling function 185 causes the yellow enclosure 25b to be displayed over the ultrasound image in the N-th frame displayed on the display 103. In addition, the display controlling function 185 causes the character string "slow" 26b to be displayed to the left side of the ultrasound image in the N-th frame displayed on the display 103.

FIG. 21 is a table illustrating another example of 25 correlation coefficients calculated in the second embodiment. In FIG. 21, the correlation coefficients that are equal to or larger than 0.0 but are smaller than the threshold value T1 are indicated with dot hatching. In the example in FIG. 21, the 25 correlation coefficients are all equal to or large than 0.0 but are smaller than the threshold value T1. In the example in FIG. 21, it is considered that the ultrasound probe 101 is either moving in a direction corresponding to one of the diagonal directions (the directions indicated with a bidirectional arrows 44 in FIGS. 18 and 19) or moving relatively fast in a direction corresponding to one of the front-and-back directions and the left-and-a right directions (the directions indicated with the bidirectional arrow 42 in FIGS. 18 and 19).

In this manner, in the example in FIG. 21, when the ultrasound probe 101 is moving in a direction corresponding to a diagonal direction, it is unclear whether the moving speed of the ultrasound probe 101 is relatively high, relatively low, or not too low, not too high, and appropriate. Accordingly, in the example in FIG. 21, the moving speed information generating function 186 does not calculate the moving speed information.

FIG. 22 is a table illustrating yet another example of 25 correlation coefficients calculated in the second embodiment. In FIG. 22, the correlation coefficients that are in the range from the threshold value T1 to the threshold value T2, inclusive, are not indicated with hatching. In the example in FIG. 22, among the 25 correlation coefficients, five correlation coefficients, namely, r11, r22, r33, r44, and r55 are in the range from the threshold value T1 to the threshold value T2, inclusive. In other words, the correlation coefficients between a region 51 and a region 52 in mutually the same position are in the range from the threshold value T1 to the threshold value T2, inclusive. Further, the 20 other correlation coefficients are equal to or larger than 0.0 but are smaller than the threshold value T1. In other words, the correlation coefficients between a region 51 and a region 52 that are not mutually in the same position are equal to or larger than 0.0 but are smaller than the threshold value T1. In the example in FIG. 22, it is considered that the ultrasound probe 101 is moving at an appropriate speed in a direction corresponding to either of the front-and-back directions.

Accordingly, the moving speed information generating function 186 generates the information indicating the enclosure 25c in the default color. As explained herein, the moving speed information generating function 186 is configured to generate the moving speed information on the basis of the 25 calculated correlation coefficients. Further, the display controlling function 185 is configured to cause the enclosure 25c in the default color to be displayed over the ultrasound image in the N-th frame displayed on the display 103.

FIG. 23 is a table illustrating yet another example of 25 correlation coefficients calculated in the second embodiment. In the example in FIG. 23, among the 25 correlation coefficients, four correlation coefficients, namely, r12, r23, r34, and r45, are larger than the threshold value T2. Further, the 21 other correlation coefficients are equal to or larger than 0.0 but are smaller than the threshold value T1.

In the example in FIG. 23, in the duration from the (N−3)th frame to the N-th frame, it is considered that, for example, the ultrasound probe 101 moved in the direction from the position in real space corresponding to the region 51_2 to the position in real space corresponding to the region 52_1, by the distance from the position in real space corresponding to the region 51_2 to the position in real space corresponding to the region 52_1. Accordingly, it is considered that the ultrasound probe 101 is moving in the direction corresponding to the direction to the left. However, the magnitude of the moving speed of the ultrasound probe 101 is unclear.

To cope with this situation, the moving speed information generating function 186 is configured to calculate the moving speed and moving speed information by using the following method.

Figures 24, 25:
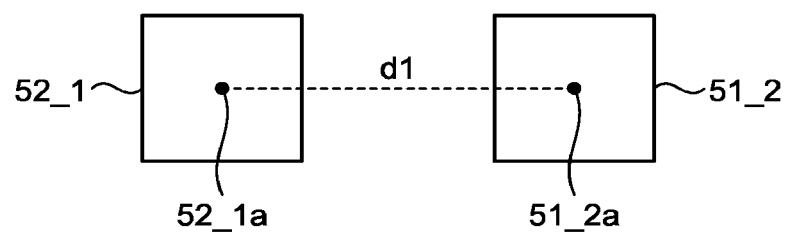
FIG. 24 is a drawing for explaining an example of a process performed by the moving speed information generating function according to the second embodiment.
FIG. 25 is a table illustrating yet another example of 25 correlation coefficients calculated in the second embodiment.

FIG. 24 is a drawing for explaining an example of a process performed by the moving speed information generating function 186 according to the second embodiment. For example, as illustrated in FIG. 24, the moving speed information generating function 186 calculates a distance d1 in the image space of the ultrasound image data between the region 52_1 and the region 51_2 corresponding to the correlation coefficient r12. For example, the moving speed information generating function 186 calculates the distance d1 between the center 52_1a of the region 52_1 and the center 51_2a of the region 51_2. After that, the moving speed information generating function 186 converts the distance d1 to a distance in real space.

Similarly, the moving speed information generating function 186 calculates the distance in the image space of the ultrasound image data between the region 52_2 and the region 51_3 corresponding to the correlation coefficient r23 and converts the calculated distance into a distance in real space. Also, the moving speed information generating function 186 calculates the distance in the image space of the ultrasound image data between the region 52_3 and the region 51_4 corresponding to the correlation coefficient r34 and converts the calculated distance into a distance in real space. Furthermore, the moving speed information generating function 186 calculates the distance in the image space of the ultrasound image data between the region 52_4 and the region 51_5 corresponding to the correlation coefficient r45 and converts the calculated distance into a distance in real space. In this manner, the moving speed information generating function 186 is configured to calculate the four distances (the distances in real space) corresponding to the four correlation coefficients r12, r23, r34, and r45.

Further, the moving speed information generating function 186 calculates the average value of the four calculated distances (the distances in real space) as a distance d2 by which the ultrasound probe 101 has moved in real space in the duration from the (N−3)th frame to the N-th frame.

After that, the moving speed information generating function 186 generates moving speed information on the basis of the distance d2.

Next, a specific example of a method for generating the moving speed information will be explained. For example, the moving speed information generating function 186 identifies a time period t1 required by the moving of the ultrasound probe 101 in the duration from the (N−3)th frame to the N-th frame. More specifically, as the time period t1, the moving speed information generating function 186 identifies the time difference between the time at which the ultrasound image data in the (N−3)th frame was generated and the time at which the ultrasound image data in the N-th frame was generated.

After that, the moving speed information generating function 186 calculates a moving speed v1 (d2/t1) of the ultrasound probe 101, by dividing the distance d2 by the time period t1.

Subsequently, the moving speed information generating function 186 judges whether or not the moving speed v1 is higher than a threshold value T3. When the moving speed v1 is determined to be higher than the threshold value T3, because the moving speed v1 is relatively high, the moving speed information generating function 186 generates the information indicating the red enclosure 25a. Further, the display controlling function 185 causes the red enclosure 25a to be displayed over the ultrasound image in the N-th frame displayed on the display 103.

In addition, when the moving speed v1 is determined to be higher than the threshold value T3, the moving speed information generating function 186 generates the character string "fast" 26a as moving speed information. After that, the display controlling function 185 causes the character string "fast" 26a to be displayed to the left side of the ultrasound image in the N-th frame displayed on the display 103.

On the contrary, when the moving speed v1 is determined to be equal to or lower than the threshold value T3, the moving speed information generating function 186 judges whether or not the moving speed v1 is lower than a threshold value T4. The threshold value T4 is smaller than the threshold value T3. When the moving speed v1 is determined to be lower than the threshold value T4, because the moving speed v1 is relatively low, the moving speed information generating function 186 generates the information indicating the yellow enclosure 25b. After that, the display controlling function 185 causes the yellow enclosure 25b to be displayed over the ultrasound image in the N-th frame displayed on the display 103.

In addition, when the moving speed v1 is determined to be lower than the threshold value T4, the moving speed information generating function 186 generates the character string "slow" 26b as moving speed information. After that, the display controlling function 185 causes the character string "slow" 26b to be displayed to the left side of the ultrasound image in the N-th frame displayed on the display 103.

On the contrary, when the moving speed v1 is determined to be equal to or higher than the threshold value T4, i.e., when the moving speed v1 is in the range from the threshold value T4 to the threshold value T3, inclusive, because the moving speed v1 is not too low, not too high, and is appropriate, the moving speed information generating function 186 generates the information indicating the enclosure 25c in the default color. After that, the display controlling function 185 causes the enclosure 25c in the default color to be displayed over the ultrasound image in the N-th frame displayed on the display 103.

FIG. 25 is a table illustrating yet another example of 25 correlation coefficients calculated in the second embodiment. In the example in FIG. 25, among the 25 correlation coefficients, two correlation coefficients, namely r41 and r52, are larger than the threshold value T2. In contrast, the 23 other correlation coefficients are equal to or larger than 0.0 but are smaller than the threshold value T1.

In the example in FIG. 25, it is considered that, in the duration from the (N−3)th frame to the N-th frame, the ultrasound probe 101 moved in the direction from the position in real space corresponding to the region 51_1 to the position in real space corresponding to the region 52_4, by the distance from the position in real space corresponding to the region 51_1 to the position in real space corresponding to the region 52_4. Accordingly, it is considered that the ultrasound probe 101 is moving in the direction corresponding to the direction to the right; however, the magnitude of the moving speed of the ultrasound probe 101 is unclear.

To cope with this situation, similarly to the example in FIGS. 23 and 24 explained above, the moving speed information generating function 186 calculates the moving speed and moving speed information. Further, similarly to the example in FIGS. 23 and 24 explained above, the display controlling function 185 causes the display 103 to display the moving speed information.

The ultrasound diagnosis apparatus 1 according to the second embodiment has thus been explained. By using the ultrasound diagnosis apparatus 1 according to the second embodiment, it is possible, similarly to the first embodiment, to enable the operator to understand the moving speed of the ultrasound probe 101, without using a detector such as a magnetic sensor that detects the moving speed of the ultrasound probe 101.

First Modification Example of Second Embodiment

In the second embodiment above, the example was explained in which the moving speed information generating function 186 calculates the moving speed v1 and calculates the moving speed information on the basis of the calculated moving speed v1. However, the moving speed information generating function 186 may calculate the moving speed information without calculating the moving speed v1. Thus, this modification example will be explained as a first modification example of the second embodiment.

For instance, in the example in FIG. 23, it is considered that, in the duration from the (N−3)th frame to the N-th frame, the ultrasound probe 101 moved by the distance from the position in real space corresponding to the region 51_2, to the position in real space corresponding to the region 52_1, for example. In other words, it is considered that the ultrasound probe 101 moved by the distance corresponding to one region. Further, in the example in FIG. 25, it is considered that, in the duration from the (N−3)th frame to the N-th frame, the ultrasound probe 101 moved by the distance from the position in real space corresponding to the region 51_1, to the position in real space corresponding to the region 52_4, for example. In other words, it is considered that the ultrasound probe 101 moved by the distance corresponding to three regions.

Accordingly, the moving speed information generating function 186 generates moving speed information in accordance with the number of regions across which the ultrasound probe 101 moved (hereinafter, "the number of regions corresponding to the moving of the ultrasound probe 101"), in the duration from the (N−3)th frame to the N-th frame. For example, the moving speed information generating function 186 judges whether or not the number of regions corresponding to the moving of the ultrasound probe 101 in the duration from the (N−3)th frame to the N-th frame is equal to or larger than a threshold value T5 (e.g., 3).

When the number of regions corresponding to the moving of the ultrasound probe 101 is determined to be equal to or larger than the threshold value T5, the moving speed of the ultrasound probe 101 is considered to be relatively high. Accordingly, in this situation, the moving speed information generating function 186 generates the information indicating the red enclosure 25a. Further, the moving speed information generating function 186 generates the character string "fast" 26a. In this manner, the moving speed information generating function 186 is configured to generate the moving speed information on the basis of the 25 calculated correlation coefficients. After that, the display controlling function 185 causes the red enclosure 25a to be displayed over the ultrasound image in the N-th frame displayed on the display 103. In addition, the display controlling function 185 causes the character string "fast" 26a to be displayed to the left side of the ultrasound image in the N-th frame displayed on the display 103.

On the contrary, when the number of regions corresponding to the moving of the ultrasound probe 101 is determined to be smaller than the threshold value T5, the moving speed information generating function 186 judges whether or not the number of regions corresponding to the moving of the ultrasound probe 101 is smaller than a threshold value T6 (e.g., 2). The threshold value T6 is smaller than the threshold value T5. When the number of regions corresponding to the moving of the ultrasound probe 101 is determined to be smaller than the threshold value T6, the moving speed of the ultrasound probe 101 is considered to be relatively low. Accordingly, in this situation, the moving speed information generating function 186 generates the information indicating the yellow enclosure 25b. In addition, the moving speed information generating function 186 generates the character string "slow" 26b. As explained herein, the moving speed information generating function 186 is configured to generate the moving speed information on the basis of the 25 calculated correlation coefficients. Further, the display controlling function 185 causes the yellow enclosure 25b to be displayed over the ultrasound image in the N-th frame displayed on the display 103. In addition, the display controlling function 185 causes the character string "slow" 26b to be displayed to the left side of the ultrasound image in the N-th frame displayed on the display 103.

In contrast, when the number of regions corresponding to the moving of the ultrasound probe 101 is determined to be equal to or larger than the threshold value T6, i.e., when the number of regions corresponding to the moving of the ultrasound probe 101 is equal to or larger than the threshold value T6 but is smaller than the threshold value T5, it is considered that the moving speed of the ultrasound probe 101 is not too low, not too high, and is appropriate. Accordingly, in this situation, the moving speed information generating function 186 generates the information indicating the enclosure 25c in the default color. As explained herein, the moving speed information generating function 186 is configured to generate the moving speed information on the basis of the 25 calculated correlation coefficients. Further, the display controlling function 185 causes the enclosure 25c in the default color to be displayed over the ultrasound image in the N-th frame displayed on the display 103.

The first modification example of the second embodiment has thus been explained. In the first modification example of the second embodiment, the ultrasound diagnosis apparatus 1 is configured to calculate the moving speed information without calculating the moving speed v1. Consequently, according to the first modification example of the second embodiment, it is possible to reduce the processing load at the time of calculating the moving speed information. Further, according to the first modification example of the second embodiment, it is possible, similarly to the first embodiment, to enable the operator to understand the moving speed of the ultrasound probe 101, without using a detector such as a magnetic sensor or the like that detects the moving speed of the ultrasound probe 101.

Second Modification Example of Second Embodiment

In the second embodiment above, the example was explained in which the moving speed information generating function 186 calculates the correlation coefficients with respect to all the sets each made up of one of the plurality of regions 51_1 to 51_m and one of the plurality of regions 52_1 to 52_m; however, it is sufficient when the moving speed information generating function 186 calculates a correlation coefficient with respect to at least one selected from among all the sets each made up of one of the plurality of regions 51_1 to 51_m and one of the plurality of regions 52_1 to 52_m. Further, the moving speed information generating function 186 may generate moving speed information on the basis of the calculated correlation coefficient. Thus, this modification example will be explained as a second modification example of the second embodiment.

In this situation, according to purposes, it is possible to change, as appropriate, with respect to which set among all the sets described above, the correlation coefficient is to be used for the judging process. For example, in the second modification example of the second embodiment, when the purpose is to enable the operator to understand only whether or not the ultrasound probe 101 is stationary, information expressing the purpose (purpose information) is input to the apparatus main body 100 via the input device 102. Further, when the purpose information is input to the apparatus main body 100, the moving speed information generating function 186 is configured to select, with respect to which set among all the sets described above, the correlation coefficient is to be calculated, in accordance with the purpose information. For example, when the purpose information indicates the abovementioned purpose, the moving speed information generating function 186 selects to calculate one correlation coefficient of one set made up of one region 51 and one region 52 in the same position as the one region 51. Further, in accordance with the selected result, the moving speed information generating function 186 calculates the one correlation coefficient of the one set made up of the one region 51 and the one region 52 that is in the same position as that of the region 51. In the following sections, the example in which the moving speed information generating function 186 calculates the one correlation coefficient of the one set will be explained.

Subsequently, the moving speed information generating function 186 judges whether or not the one calculated correlation coefficient is larger than the threshold value T2. When the one correlation coefficient is larger than the threshold value T2, the moving speed information generating function 186 generates the information indicating the yellow enclosure 25b. In addition, when the one correlation coefficient is larger than the threshold value T2, the moving speed information generating function 186 generates the character string "slow" 26b. As explained herein, the moving speed information generating function 186 is configured to generate the moving speed information on the basis of the one calculated correlation coefficient. Further, the display controlling function 185 causes the yellow enclosure 25b to be displayed over the ultrasound image in the N-th frame displayed on the display 103. In addition, the display controlling function 185 causes the character string "slow" 26b to be displayed to the left side of the ultrasound image in the N-th frame displayed on the display 103.

The second modification example of the second embodiment has thus been explained. In the second modification example of the second embodiment, the moving speed information generating function 186 is configured to calculate the correlation coefficient with respect to at least one set selected from among all the sets each made up of one of the plurality of regions 51_1 to 51_m and one of the plurality of regions 52_1 to 52_m, in accordance with the purpose information. Consequently, according to the second modification example of the second embodiment, it is possible, in accordance with the purpose indicated by the purpose information, to prevent the occurrence of the situation where correlation coefficients are unnecessarily calculated.

Further, in the second modification example of the second embodiment, the ultrasound diagnosis apparatus 1 is configured to calculate the moving speed information without calculating the moving speed v1. Consequently, according to the second modification example of the second embodiment, it is possible to reduce the processing load at the time of calculating the moving speed information. Further, according to the second modification example of the second embodiment, it is possible, similarly to the first embodiment, to enable the operator to understand the moving speed of the ultrasound probe 101, without using a detector such as a magnetic sensor that detects the moving speed of the ultrasound probe 101.

Third Embodiment

In the embodiments described above, the example was explained in which the ultrasound diagnosis apparatus 1 is configured to detect the feature site by performing the CAD process on the ultrasound scan in a real-time manner and to display the detected feature site and the moving speed information in a real-time manner. However, another arrangement is also acceptable in which a medical image processing apparatus performs the same processes, not in a real-time manner, but after an ultrasound scan. Thus, this embodiment will be explained as a third embodiment.

Figure 26:
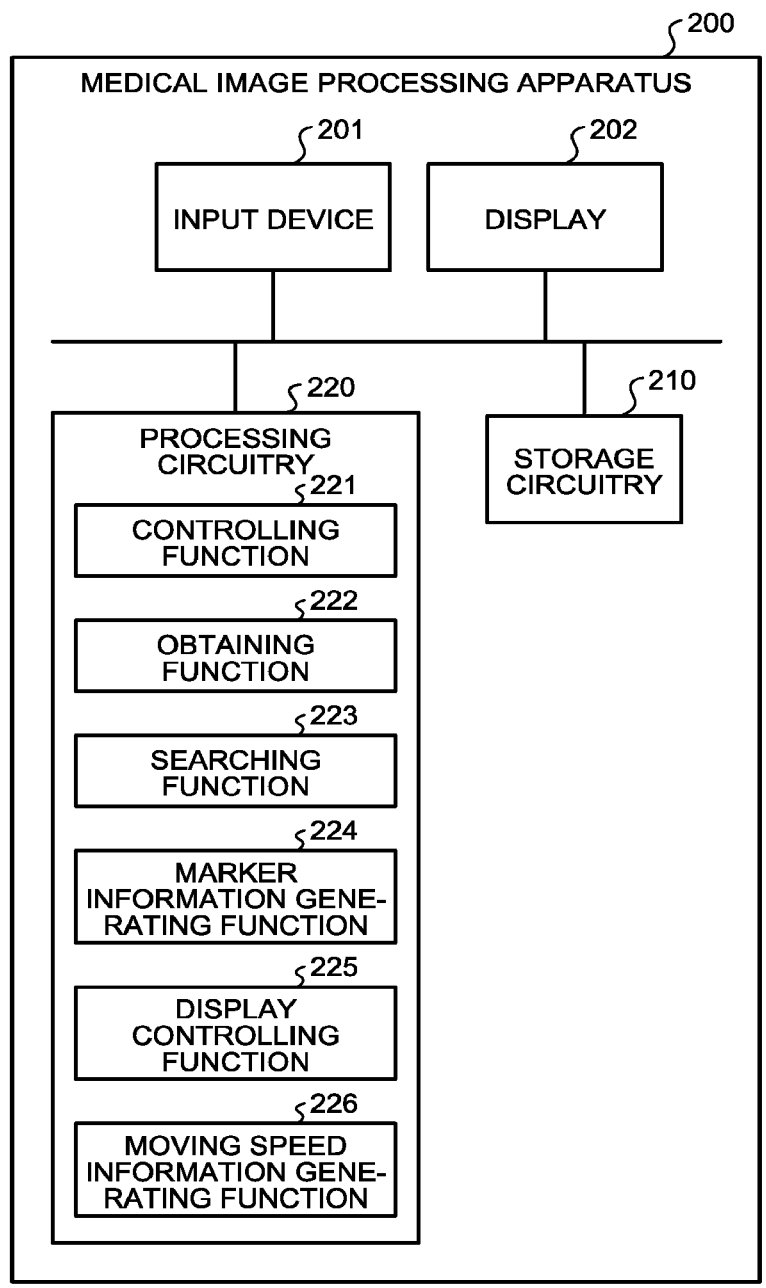
FIG. 26 is a diagram illustrating an exemplary configuration of a medical image processing apparatus according to a third embodiment.

FIG. 26 is a diagram illustrating an exemplary configuration of a medical image processing apparatus 200 according to the third embodiment. As illustrated in FIG. 26, the medical image processing apparatus 200 includes an input device 201, a display 202, storage circuitry 210, and processing circuitry 220. The input device 201, the display 202, the storage circuitry 210, and the processing circuitry 220 are connected so as to be able to communicate with one another. The medical image processing apparatus 200 is an example of the analyzing apparatus.

The input device 201 is realized by using a mouse, a keyboard, a button, a panel switch, a touch command screen, a foot switch, a trackball, a joystick, and/or the like. The input device 201 is configured to receive various types of setting requests from an operator of the medical image processing apparatus 200. The input device 201 is configured to output the received various types of setting requests to the processing circuitry 220. For example, the input device 201 is configured to receive an instruction (an execution instruction) to execute the CAD process from the operator of the medical image processing apparatus 200 and to output the received execution instruction to the processing circuitry 220. Further, via the input device 201, the operator is also able to set a ROI, which is a search range for a feature site, in an ultrasound image during the CAD process.

The display 202 is, for example, configured to display medical images and a Graphical User Interface (GUI) used by the operator for inputting the various types of setting requests via the input device 201.

The storage circuitry 210 is configured to store therein various types of programs for displaying the GUI and information used by the programs. Further, the storage circuitry 210 is configured to store therein the plurality of pieces of ultrasound image data in a time series generated by the ultrasound diagnosis apparatus 1.

The processing circuitry 220 is configured to control the entirety of processes performed by the medical image processing apparatus 200. The processing circuitry 220 is realized by using a processor, for example. As illustrated in FIG. 26, for example, the processing circuitry 220 has processing functions, namely, a controlling function 221, an obtaining function 222, a searching function 223, a marker information generating function 224, a display controlling function 225, and a moving speed information generating function 226. In this situation, for example, the processing functions of the constituent elements of the processing circuitry 220 illustrated in FIG. 26, namely the controlling function 221, the obtaining function 222, the searching function 223, the marker information generating function 224, the display controlling function 225, and the moving speed information generating function 226, are recorded in the storage circuitry 210 in the form of computer-executable programs. The processing circuitry 220 is a processor that realizes the functions corresponding to the programs by reading and executing the programs from the storage circuitry 210. In other words, the processing circuitry 220 that has read the programs has the functions illustrated within the processing circuitry 220 in FIG. 26.

For example, the medical image processing apparatus 200 is configured to obtain the plurality of pieces of ultrasound image data in a time series generated by the ultrasound diagnosis apparatus 1. Further, by performing the same processes as those performed by the ultrasound diagnosis apparatus 1 according to the first or the second embodiment on the ultrasound image data, the medical image processing apparatus 200 is configured to cause the display 202 to display the ultrasound images, the detected feature site, and the moving speed information.

The controlling function 221 is configured to control the entirety of the processes performed by the medical image processing apparatus 200. The obtaining function 222 has the same functions as those of the obtaining function 182 described above. The searching function 223 has the same functions as those of the searching function 183 described above. The marker information generating function 224 is configured to execute the same functions as those of the marker information generating function 184 described above. The display controlling function 185 is configured to execute the same functions as those of the display controlling function 185 described above.

The medical image processing apparatus 200 according to the third embodiment has thus been explained. By using the medical image processing apparatus 200 according to the third embodiment, it is possible, similarly to the first and the second embodiments, to enable the operator to understand the moving speed of the ultrasound probe 101, without using a detector such as a magnetic sensor that detects the moving speed of the ultrasound probe 101.

According to at least one aspect of the embodiments and the modification examples described above, it is possible to enable the operator to understand the moving speed of the ultrasound probe 101, without using a detector such as a magnetic sensor that detects the moving speed of the ultrasound probe 101.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:
1. An ultrasound diagnosis apparatus, comprising:
processing circuitry configured to
generate moving speed information indicating a moving speed of an ultrasound probe, based on a predetermined number of pieces of medical image data among a plurality of pieces of medical image data in a time series obtained from an ultrasound scan performed by the ultrasound probe; and
cause a display to display the moving speed information in a real-time manner,
wherein the processing circuitry is further configured to
set a search range in each of a plurality of medical images respectively represented by the plurality of pieces of medical image data, and search for a feature site in the search range set in each of the plurality of medical images,
generate, as the moving speed information, information that indicates an enclosure indicating the search range and of which a display mode varies in accordance with the moving speed, and
generate marker information when it is determined, based on a result of searching for the feature site, that the feature site in the search range is detected.

2. The ultrasound diagnosis apparatus according to claim 1, wherein the processing circuitry is further configured to generate the moving speed information based on two pieces of medical image data serving as the predetermined number of pieces of medical image data.

3. The ultrasound diagnosis apparatus according to claim 2, wherein the processing circuitry is further configured to cut out a region from each of the two pieces of medical image data, calculate a correlation coefficient between the region cut out from one of the two pieces of medical image data and the region cut out from the other piece of medical image data, and generate the moving speed information based on the correlation coefficient.

4. The ultrasound diagnosis apparatus according to claim 3, wherein the processing circuitry is further configured to cut out a plurality of regions in a plurality of mutually-same positions in an image space of the medical image data from the two pieces of medical image data, calculate a plurality of correlation coefficients with respect to the plurality of mutually-same positions, and generate the moving speed information based on a statistical value of the calculated plurality of correlation coefficients.

5. The ultrasound diagnosis apparatus according to claim 2, wherein the processing circuitry is further configured to cut out a plurality of first regions from one of the two pieces of medical image data, cut out a plurality of second regions from the other piece of medical image data, calculate, with respect to at least one set made up of a first region and a second region, a correlation coefficient between the first region and the second region, and generate the moving speed information based on the correlation coefficient calculated with respect to said at least one set.

6. The ultrasound diagnosis apparatus according to claim 5, wherein, with respect to all sets, each made up of a first region and a second region, the processing circuitry is further configured to calculate a correlation coefficient between the first region and the second region, and generate the moving speed information based on the correlation coefficients calculated with respect to all the sets.

7. The ultrasound diagnosis apparatus according to claim 5, wherein, with respect to one set made up of a first region and a second region, the processing circuitry is further configured to calculate the correlation coefficient between the first region and the second region, and generate the moving speed information based on the correlation coefficient calculated with respect to the one set.

8. The ultrasound diagnosis apparatus according to claim 1, wherein the processing circuitry is further configured to select the predetermined number of pieces of medical image data used for generating the moving speed information in accordance with a frame rate of the plurality of pieces of medical image data, and generate the moving speed information based on the selected predetermined number of pieces of medical image data.

9. The ultrasound diagnosis apparatus according to claim 1, wherein the processing circuitry is further configured to determine a relative moving speed of the moving speed of the ultrasound probe based on the predetermined number of pieces of medical image data, and
wherein the processing circuitry is further configured to cause the display to display the relative moving speed as the moving speed information.

10. The ultrasound diagnosis apparatus according to claim 9, wherein the moving speed information indicating the relative moving speed comprises a first color for faster speeds and a second color for slower speeds relative to the faster speeds.

11. The ultrasound diagnosis apparatus according to claim 9, wherein the moving speed information indicating the relative moving speed comprises first text for faster speeds and second text for slower speeds relative to the faster speeds.

12. The ultrasound diagnosis apparatus of claim 1, wherein the processing circuitry is further configured to cause the display to display a marker image based on the generated marker information, the marker image indicating a location of the detected feature site.

13. The ultrasound diagnosis apparatus of claim 12, wherein the processing circuitry is further configured to cause the display to display the marker image, which encloses the detected feature site.

* * * * *